US006678543B2

(12) United States Patent
Diab et al.

(10) Patent No.: US 6,678,543 B2
(45) Date of Patent: Jan. 13, 2004

(54) OPTICAL PROBE AND POSITIONING WRAP

(75) Inventors: Mohamed Kheir Diab, Mission Viejo, CA (US); Massi E. Kiani, Laguna Niguel, CA (US); Charles Robert Ragsdale, Newport Beach, CA (US); James M. Lepper, Jr., Trabuco Canyon, CA (US)

(73) Assignee: Masimo Corporation, Irvine, CA (US)

( * ) Notice: Subject to any disclaimer, the term of this patent is extended or adjusted under 35 U.S.C. 154(b) by 64 days.

(21) Appl. No.: 10/005,711

(22) Filed: Nov. 8, 2001

(65) Prior Publication Data

US 2002/0062071 A1 May 23, 2002

Related U.S. Application Data

(63) Continuation of application No. 09/451,151, filed on Nov. 30, 1999, now Pat. No. 6,397,091, which is a continuation of application No. 09/016,924, filed on Feb. 2, 1998, now Pat. No. 6,011,986, which is a continuation of application No. 08/478,493, filed on Jun. 7, 1995, now Pat. No. 5,758,644.

(51) Int. Cl.[7] .................................................. A61B 5/00
(52) U.S. Cl. ...................................... 600/323; 600/344
(58) Field of Search ................................. 600/310, 322, 600/323, 326, 333, 344; 439/492, 499

(56) References Cited

U.S. PATENT DOCUMENTS

| 3,463,142 | A |   | 8/1969  | Harte et al.        |         |
|-----------|---|---|---------|---------------------|---------|
| 3,647,299 | A |   | 3/1972  | Lavallee            |         |
| 3,740,570 | A |   | 6/1973  | Kaelin et al.       |         |
| 3,799,672 | A |   | 3/1974  | Vurek               |         |
| 4,086,915 | A |   | 5/1978  | Kofsky et al.       |         |
| 4,169,976 | A |   | 10/1979 | Cirri               |         |
| 4,182,977 | A |   | 1/1980  | Stricklin, Jr.      |         |
| 4,308,456 | A |   | 12/1981 | Van Der Gaag et al. |         |
| 4,346,590 | A |   | 8/1982  | Brown               |         |
| 4,407,290 | A |   | 10/1983 | Wilber              |         |
| 4,449,821 | A |   | 5/1984  | Lee                 |         |
| 4,480,886 | A | * | 11/1984 | Bergamin            | 439/492 |
| 4,580,867 | A | * | 4/1986  | Wright et al.       | 439/260 |
| 4,621,643 | A |   | 11/1986 | New, Jr. et al.     |         |
| 4,653,498 | A |   | 3/1987  | New, Jr. et al.     |         |
| 4,700,708 | A |   | 10/1987 | New, Jr. et al.     |         |
| 4,770,179 | A |   | 9/1988  | New, Jr. et al.     |         |
| 4,848,901 | A |   | 7/1989  | Hood, Jr.           |         |
| 4,877,322 | A |   | 10/1989 | Hill                |         |
| 4,913,150 | A |   | 4/1990  | Cheung et al.       |         |
| 4,942,877 | A |   | 7/1990  | Sakai et al.        |         |

(List continued on next page.)

FOREIGN PATENT DOCUMENTS

| EP | 019 478  | 11/1980 |
| JP | 5275746  | 10/1993 |
| WO | 88/10462 | 12/1988 |

OTHER PUBLICATIONS de Kock, J.P. et al., "The Effect of Varying LED Intensity on Pulse Oximeter Accuracy", *Journal of Medical Engineering & Technology*, vol. 15, No. 3, May/Jun. 1991, pp. 111–116.

Reynolds, K.J., et al., "Temperature Dependence of LED and its Theoretical Effect on Pulse Oximetry", *British Journal & Anaesthesia*, 1991, vol., 67, pp. 638–643.

*Primary Examiner*—Eric F. Winakur
(74) *Attorney, Agent, or Firm*—Knobbe, Martens Olson & Bear LLP

(57) ABSTRACT

Embodiments of the present disclosure include an oximeter sensor system including a reusable portion including a substantially rigid connector connected to an end of a cable. The substantially rigid connector includes an electronic element housing at least one electronic component of a probe. The system also includes a disposable portion including a flexible wrap comprising a substantially rigid connection port shaped to receive the substantially rigid connector in a releasably securable manner.

15 Claims, 20 Drawing Sheets

U.S. PATENT DOCUMENTS

| | | |
|---|---|---|
| 5,058,588 A | 10/1991 | Kaestle |
| 5,113,862 A | 5/1992 | Mortazavi |
| 5,140,228 A | 8/1992 | Biegel |
| 5,209,230 A * | 5/1993 | Swedlow et al. ............ 600/344 |
| 5,246,003 A * | 9/1993 | DeLonzor ................... 600/344 |
| 5,249,576 A * | 10/1993 | Goldberger et al. ........ 600/323 |
| 5,267,562 A | 12/1993 | Ukawa et al. |
| 5,287,853 A | 2/1994 | Vester et al. |
| 5,308,919 A | 5/1994 | Minnich |
| 5,397,247 A * | 3/1995 | Aoki et al. .................. 439/496 |
| 5,515,169 A | 5/1996 | Cargill et al. |
| 5,758,644 A | 6/1998 | Diab et al. |
| 6,144,868 A | 11/2000 | Parker |

\* cited by examiner

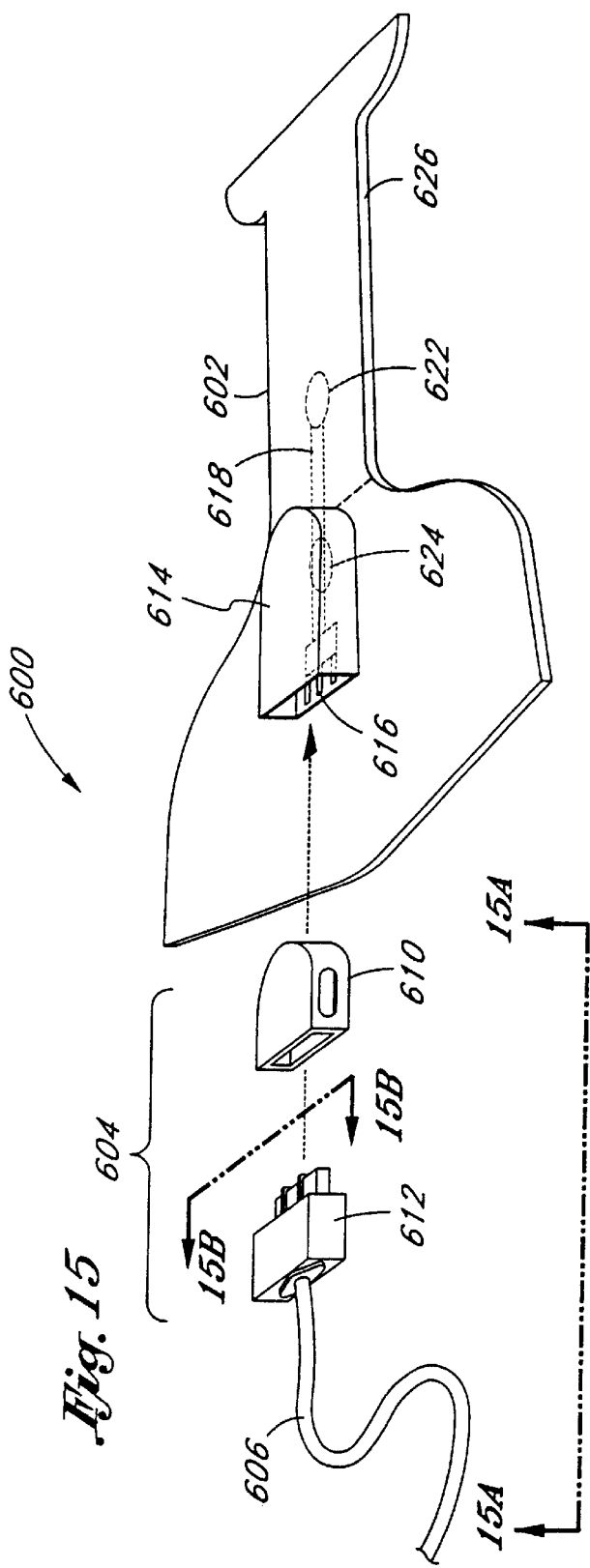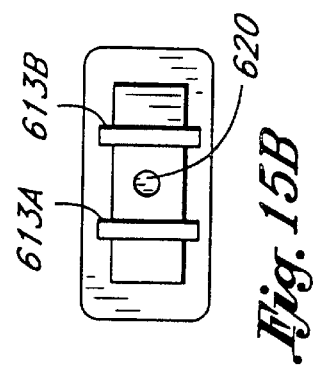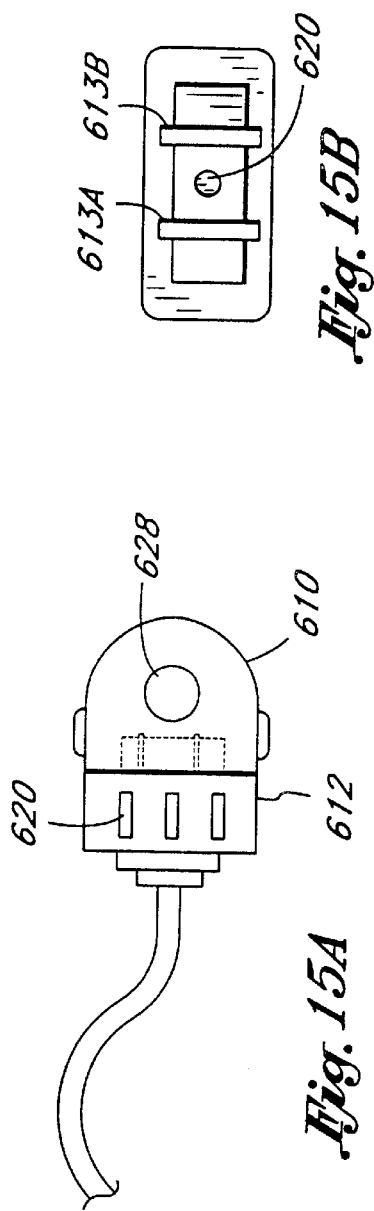

OPTICAL PROBE AND POSITIONING WRAP

RELATED APPLICATIONS

This application is a continuation of U.S. patent application Ser. No. 09/451,151, filed Nov. 30, 1999, now U.S. Pat. No. 6,397,091, which is a continuation of U.S. patent application Ser. No. 09/016,924, filed on Feb. 2, 1998, now U.S. Pat. No. 6,011,986, which is a continuation of U.S. patent application Ser. No. 08/478,493, filed on Jun. 7, 1995, now U.S. Pat. No. 5,758,644.

BACKGROUND OF THE INVENTION

1. Field of the Invention

The present invention relates generally to more effective calibration and use of light-emitting diodes. More particularly, the present invention relates to an apparatus and method of calibrating and using light-emitting diodes in a sensor for use with an oximeter system.

2. Description of the Related Art

Light-emitting diodes (LEDs) are used in many applications. In certain applications, knowledge of the particular wavelength of operation of the LED is required to obtain accurate measurements. One such application is noninvasive oximeters conventionally used to monitor arterial oxygen saturation.

In conventional oximetry procedures to determine arterial oxygen saturation, light energy is transmitted from LEDs, each having a respective wavelength, through human tissue carrying blood. Generally, the LEDs are part of a sensor attached to an oximeter system. In common usage, the sensor is attached to a finger or an earlobe. The light energy, which is attenuated by the blood, is detected with a photodetector and analyzed to determine the oxygen saturation. Additional constituents and characteristics of the blood, such as the saturation of carboxyhemoglobin and scattering can be monitored by utilizing additional LEDs with additional wavelengths.

U.S. Pat. No. 4,653,498 to New, Jr., et al., discloses a pulse oximeter that utilizes two LEDs to provide incident light energy of two different, but carefully selected, wavelengths.

In conventional oximeters, the wavelength of each LED in a sensor must be precisely known in order to calculate accurately the oxygen saturation. However, the sensors are detachable from the oximeter system to allow for replacement or disinfection.

When a sensor is replaced, the LEDs of the new sensor may have a slightly different wavelength for the predetermined LED drive current due to manufacturing tolerances. Accordingly, conventional oximeters provide for indicating to the oximeter the particular wavelength of the LEDs for a given sensor. In one known system, a resistor is used to code each transmission LEDs. The resistor is selected to have a value indicative of the wavelength of the LED. The oximeter reads the resistor value on the sensor and utilizes the value of the resistor to determine the actual wavelength of the LEDs. This calibration procedure is described in U.S. Pat. No. 4,621,643, assigned to Nellcor, Inc. Such a prior art sensor is depicted in FIG. 1.

SUMMARY OF THE INVENTION

In conventional oximeters which provide an indication of the operational wavelength of each LED for each sensor, the oximeter systems are programmed to perform the desired calculations for various wavelengths. This complicates the design of the oximeter system, and therefore, adds expense to the oximeter system. Accordingly, it would be advantageous to provide sensors which exhibit the same wavelength characteristics from sensor to sensor.

In addition, conventional sensors require an additional LED for each additional wavelength desired. For replaceable sensors, each LED can add significant total additional cost because of the large number of sensors that are used in hospitals and the like. Therefore, it would be desirable to provide a sensor which provides more than one wavelength from a single LED.

Many LEDs are observed to exhibit a wavelength shift in response to a change in drive current, drive voltage, temperature, or other tuning parameters such as light directed on the LED. The present invention involves an improved method and apparatus to calibrate LEDs by utilizing this wavelength shift. In addition, the present invention involves utilizing the wavelength shift to allow a single LED to provide more than one operating wavelength. The addition of a wavelength provides the ability to monitor additional parameters in a medium under test without adding an LED. In oximetry, this allows monitoring of additional constituents in the blood without adding additional LEDs to the oximeter sensor.

The present invention also involves an application of the wavelength shift in LEDs to obtain physiological data regarding the oxygen saturation of blood without knowing the precise operational wavelength of an LED in the sensor.

One aspect of the present invention provides a tuned light transmission network for transmitting light energy at a preselected wavelength. The network has a current source configured to provide a preselected source current with a light emitting diode coupled to the current source. The light emitting diode is of the type that exhibits a shift in wavelength with a shift in a selected tuning parameter. Advantageously, the tuning parameter is drive current or drive voltage. A tuning resistor connected in parallel with the light emitting diode has a value selected to draw at least a first portion of the preselected source current such that a second portion of the preselected source current passes through the light emitting diode. The second portion of the preselected source current is selected to cause the light emitting diode to generate light energy of a preselected wavelength.

In the present embodiment, the tuned light transmission network also comprises a detector responsive to light energy from the light emitting diode to generate an output signal indicative of the intensity of the light energy.

Another aspect of the present invention involves a method for precalibrating a light generating sensor. The method involves a number of steps. A first level of current passing through a light source as required to operate the light source at a preselected wavelength is determined. A second level of current is then defined. The second level of current is higher than the first level of current. The second level of current forms a drive current. A resistor is then selected which when coupled in parallel with the light source forms a tuned light source network. The resistor is selected such that when it is connected in parallel with the light source, it draws a sufficient amount of the drive current such that the first level of current passes through the light source.

Another aspect of the present invention is a method of providing two wavelengths from a single light emitting diode. A light emitting diode is selected of the type that exhibits a wavelength shift with a change in drive current through the light emitting diode for a range of drive currents. A source of electrical energy is coupled to the light emitting diode to provide the drive currents. The light emitting diode is driven with a first level of drive current within the range of drive current to cause the light emitting diode to become active and operate at a first wavelength in response to the first level of drive currents. The light emitting diode is then driven with a second level of drive current within the range of drive current and different from the first level of drive current to cause the light emitting diode to become active and operate at a second wavelength in response to the second level of drive current.

In an embodiment where the light emitting diode is configured to transmit light energy to a medium under test, the method comprises further steps. While the light emitting diode is operating at the first wavelength, light is transmitted as a first light energy at the first wavelength through the medium under test. The first wavelength is chosen for a first predetermined attenuation characteristic of the light energy as it propagates through the medium under test. The attenuated light energy is measured from the light emitting diode with a photodetector. In addition, while the light emitting diode is operating at the second wavelength, light energy is transmitted at the second wavelength through the medium under test. The second wavelength is chosen for a second predetermined attenuation characteristic of the light energy as it propagates through the medium under test. The attenuated light energy is measured at the second wavelength from the light emitting diode.

In one advantageous embodiment, the method is used to determine the oxygen saturation of blood, and the medium under test comprises a portion of the human body having flowing blood. In this embodiment, the method further involves coupling the source of energy to a second light emitting diode which operates at a third wavelength distinct from the first and the second wavelengths. Further, the change in wavelength between the first and second wavelengths has a preselected value. Third light energy is transmitted at the third wavelength through the medium under test, and the third light energy is measured after propagation through the medium under test. Based upon the measurements, the oxygen saturation of the blood is determined.

In one embodiment, parameters in addition to oxygen saturation may also be determined relating to the medium under test when the first wavelength has a known value, and the change in wavelength between the first and the second wavelengths has a preselected value. In this embodiment, value of the second wavelength is determined, and another parameter is calculated relating to the blood. In one embodiment, the another parameter is the saturation of carboxyhemoglobin. Alternatively, another parameter is scattering. Yet another parameter is Methhemoglobin.

Advantageously, using the apparatus described above for tuning, the first light emitting diode is adjusted with an adjusting resistor such that the change in wavelength for an incremental change in current matches a preselected wavelength change. Preferably, adjusting involves placing the adjusting resistor in parallel with the first light emitting diode, and selecting the value of the adjusting resistor to cause the first light emitting diode to exhibit the preselected change for the incremental change in current.

Yet a further aspect of the present invention provides an oximeter sensor having a first light emitting device configured to generate a light at a first known wavelength with a resistor in parallel with the first light emitting device. Preferably, the light emitting device comprises a light emitting diode. In one embodiment, the resistor comprises an encoding resistor having a value indicative of the first known wavelength value. The value of the encoding resistor is sufficiently high such that the encoding resistor draws effectively insignificant current during active operation of the first light emitting device.

In another embodiment, the resistor comprises a security resistor having a value indicative that the oximeter sensor is of a predetermined type. In addition, the value of the security resistor is sufficiently high such that the security resistor draws effectively insignificant current during active operation of the first light emitting device.

Still a further aspect of the present invention involves a method of tuning a light emitting diode to operate at a preselected wavelength within a range of wavelengths. the method involves selecting a light emitting diode that exhibits a wavelength shift in response to a change in drive current within a range of drive current and driving the light emitting diode with a first drive current. The wavelength of the light emitting diode during operation at the first drive current is measured, and, if the light emitting diode is not operating at the preselected wavelength, the drive current is adjusted within the range of drive current to a second drive current such that the light emitting diode operates at the preselected wavelength.

Another aspect of the present invention involves a sensor configured to transmit and detect light. The sensor has at least one light emitting element, the light emitting element having an emission with a centroid transmission wavelength. The sensor further has first and second photodetectors, the emission of the light emitting element being within the response of the first and second photodetectors. A light directing member is configured to direct light from the at least one light emitting element to the first and second photodetectors. A filter positioned between the second photodetector and the at least one light emitting element has a transition band selected to encompass the centroid transmission wavelength.

In one embodiment, the sensor comprises an oximeter sensor, and the at least one light emitting element comprises first and second light emitting diodes. Advantageously, the first light emitting diode has a centroid wavelength in the red range and the second light emitting diode has a centroid wavelength in the infrared range. Advantageously, the filter has a transition band which encompasses the centroid wavelength of the first light emitting diode.

In one advantageous embodiment, the light directing member comprises an integrating optical sphere having the first and second photodetectors positioned about the sphere so as to receive substantially equivalent portions of light from the at least one light emitting element.

In another embodiment, light directing member comprises a beam splitting member positioned to substantially equally divide light from the at least one light emitting member and to direct substantially equal portions of the light to the first and the second photodetectors.

Still another aspect of the present invention involves a method of determining the centroid wavelength of a light emitting element. The method involves providing a set of a plurality of predetermined ratios, each of the plurality of predetermined ratios corresponding to an associated centroid wavelength. Light is transmitted from the light emitting element to a first light detecting element to obtain a first intensity, and light is transmitted from the light emitting element through a filter which attenuates the light to a second light detecting element to obtain a second intensity. A ratio of the second intensity to the first intensity is then calculated. The ratio is compared to the set of predetermined ratios to reference the centroid wavelength of the light emitting element.

In one embodiment, the first and second light detecting elements comprise the same light detecting element.

DETAILED DESCRIPTION OF THE PREFERRED EMBODIMENT

The present invention has applicability to the use of medical probes and LEDs in general. However, an understanding is facilitated with the following description of the application of the principles of the present invention to oximetry.

The advantages of noninvasive techniques in monitoring the arterial oxygen (or other constituents) saturation of a patient are well-known. In oximetry, light of a known wavelength is transmitted through a medium (e.g., a human digit such as a finger) under test. The light energy is partially absorbed and scattered by the constituents that make up the medium as the light propagates through the medium. The absorption and scattering of the light energy by any given constituent depends upon the wavelength of the light passing through the constituent, as well as several other parameters. The absorption by a constituent is characterized with what is known as the extinction coefficient.

Figure 2:
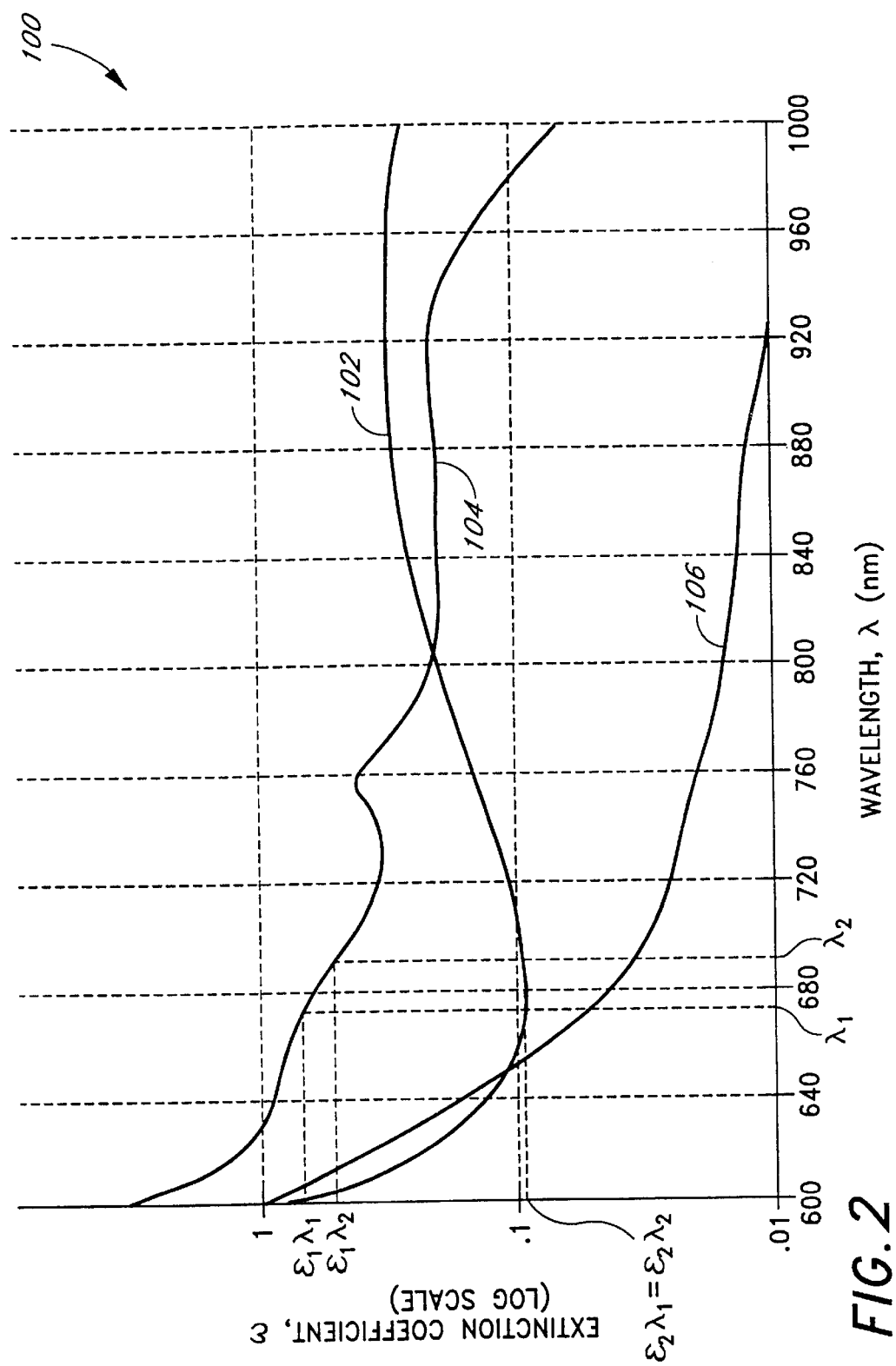
FIG. 2 depicts a representational graph illustrating the relationship between the extinction coefficients of three constituents of blood with respect to the transmission wavelength of light transmitted through the blood.

FIG. 2 represents an exemplary graph 100 of the relationship between the extinction coefficient of three possible constituents of blood with respect to the wavelength of light. Specifically, a first curve 102 illustrates the relationship between the extinction coefficient of oxyhemoglobin (oxygenated hemoglobin) with respect to the transmission wavelength; a second curve 104 illustrates the relationship between the extinction coefficient of reduced hemoglobin with respect to the transmission wavelength; and a third curve 106 illustrates the relationship between the extinction coefficient of carboxyhemoglobin (hemoglobin containing carbon monoxide) with respect to the transmission wavelength. This relationship is well understood in the art.

One wavelength is required for each separate constituent in the medium. The wavelengths used for oximetry are chosen to maximize sensitivity of the measurement (i.e., oxygen saturation, etc.). These principles are well understood in the art.

The amplitude of the energy incident on a homogeneous media having at least one constituent under test is approximately related to the amplitude of the energy transmitted through the media as follows:

$$I = I_o e^{-\sum_{i=1}^{N} d_i \epsilon_i c_i} \quad (1)$$

where $I_o$ is the energy incident on the medium, I is the attenuated signal, $d_i$ is the thickness of the $i_{th}$ constituent through which light energy passes, $\epsilon_i$ is the extinction (or absorption) coefficient of the $i_{th}$ constituent through which the light energy passes (the optical path length of the $i_{th}$ constituent), and $c_i$ is the concentration of the $i_{th}$ constituent in thickness $d_i$. As well-understood in the art, this basic relationship is utilized to obtain oxygen saturation using conventional oximetry techniques.

It should be understood that the above equation is simplified for discussion purposes. Other factors such as multiple scattering also contribute to the resulting attenuation of the light energy. Multiple scattering is discussed in a paper by Joseph M. Schmitt entitled, "Simple Photon Diffusion Analysis of the Effects of Multiple Scattering on Pulse Oximetry," *IEEE Transactions on Biomedical Engineering*. vol. 38, no. 12, December 1991.

However, for further discussion purposes, the simplified equation (1) will be utilized. In procedures based on oximetry technology, the accuracy of the physiological measurement is impacted by the accuracy of the wavelength of the transmission LEDs because, as depicted in FIG. 2, the extinction coefficient is dependent upon the wavelength of the transmission LED. In order to obtain oxygen saturation, two LEDs, one in the red wavelength range and one in the infrared wavelength range, are typically utilized in order to obtain the saturation measurement for a patient. Further, as set forth in Equation (1), the extinction coefficient is a critical variable in the equation. Accordingly, it is important that the oximeter be provided with information as to the specific wavelength of the transmission LEDs for the sensor. However, the wavelength of different LEDs, although manufactured for a specified wavelength, varies for the same drive current from LED to LED due to manufacturing tolerances.

Wavelength Tuned LEDs

Figure 3A:
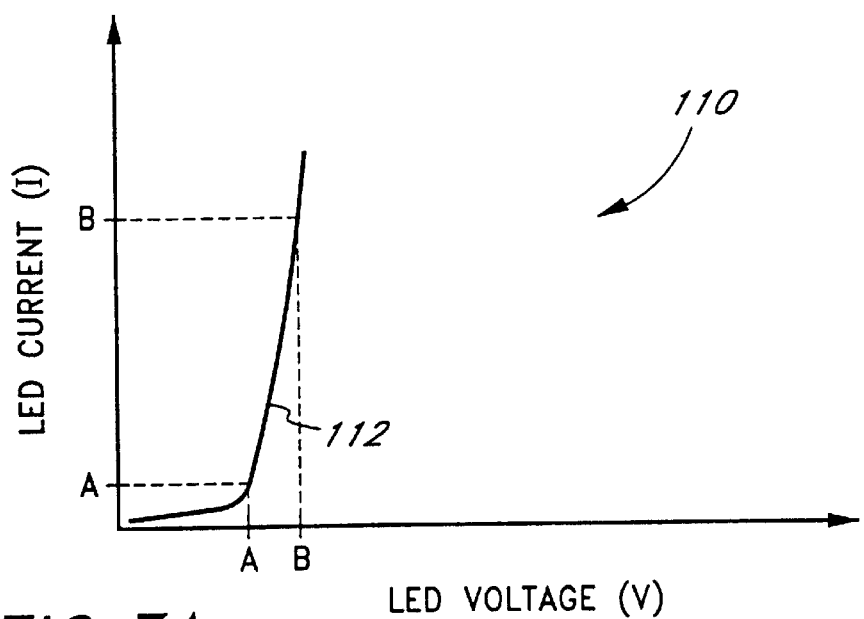
FIGS. 3A and 3B depict exemplary LED characteristics.
Figure 3B:
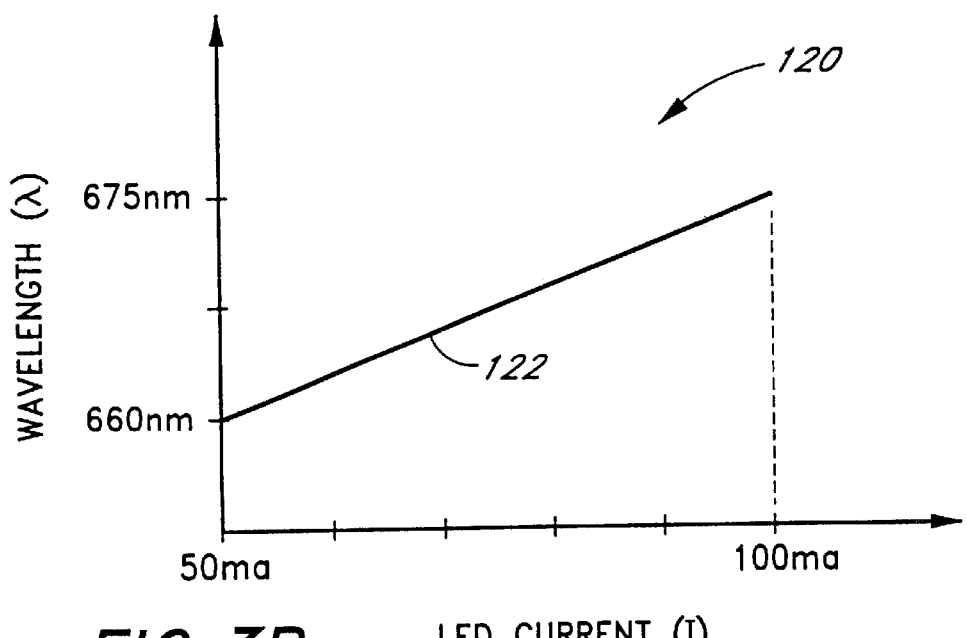

One aspect of the present invention provides an apparatus and method for tuning each LED in a sensor such that the operating wavelengths for LEDs do not vary significantly from sensor to sensor. The tuning is performed by utilizing the wavelength shift exhibited in many LEDs in response to a change in drive current. FIGS. 3A and 3B illustrate this wavelength shift principle in two graphs. The graph 110 of FIG. 3A depicts (with a curve 112) current in the vertical axis versus voltage in the horizontal axis for a typical LED.

The graph 110 of FIG. 3A is well-understood in the art. In the area referenced between the axis indicated A and B, just beyond the shoulder of the curve 112, the wavelength of certain LEDs shifts in a substantially linear fashion in response to a corresponding change in drive current or voltage. The amount of wavelength shift per incremental change in drive current typically differs for each LED (designed for the same wavelength), just as the operating wavelength for LEDs (designed for a specific wavelength) varies for the same drive current from LED to LED.

FIG. 3B depicts an exemplary graph 120 of the wavelength of an LED in response to the drive current in the area of the shoulder depicted in FIG. 3A. This graph depicts in a curve 122 an exemplary wavelength shift for an LED in the red range in response to drive current changes. The slope of the curve 122 depicted in FIG. 3B varies from LED to LED, as does the wavelength range. However, for conventional LEDs used in blood oximetry, an incremental shift in drive current through the LEDs causes some incremental shift in the wavelength. Because this relationship is substantially linear in the area just beyond the shoulder of the curve 112 depicted in FIG. 3A, in one preferred embodiment, the shift is obtained in the area beyond the shoulder. The graph of FIG. 3B is not meant to represent all LEDs, but merely to represent one possible wavelength shift corresponding to a particular change in drive current.

Accordingly, one way to obtain a selected wavelength is to drive the LEDs with the current necessary to obtain the wavelength. However, such embodiment would require an oximeter design which varies the LED drive current for each sensor.

In one advantageous embodiment, in order to avoid the added complexity of oximeter system design, a resistor is placed in parallel with an LED in order to adjust the drive current through the LED to a level which will result in a selected wavelength. In such embodiment, the oximeter system is designed to operate at the selected wavelength for each LED in the sensor. And, the oximeter need only provide a fixed drive current. Accordingly, in one embodiment, the design of the oximeter is simpler in that it need not take into account variations of wavelength from sensor to sensor. The oximeter can simply be designed to operate at the selected wavelengths and have a fixed drive current.

Figure 4A:
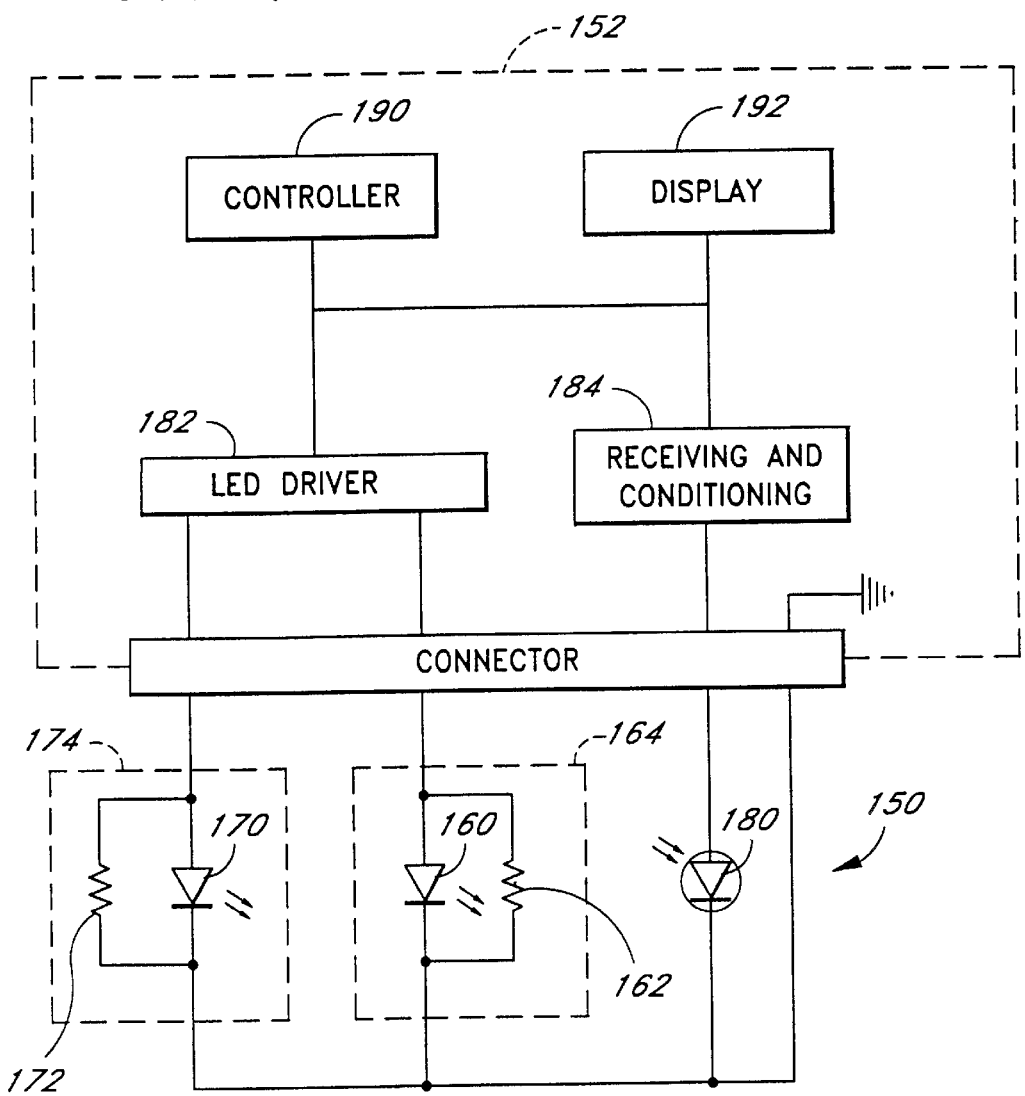
FIG. 4A depicts a representation of a tuned oximeter sensor according to one aspect of the present invention.

Each LED sensor manufactured for the oximeter is tuned, using the wavelength shift, such that the LEDs in the sensor generate light at the selected wavelengths for the oximeter. FIG. 4 depicts one embodiment of a tuned sensor 150, connected to an exemplary oximeter system 152, according to the LED tuning aspect of the present invention.

The sensor 150 is illustrated with a first light source 160 and a second light source 170, typically LEDs. A first tuning resistor 162 connected in parallel with the first LED 160 forms a first tuned LED network 164. Similarly, a second tuning resistor 172 is connected in parallel with the second LED 170 to form a second tuned LED network 174. The sensor 150 further comprises a photodetector 180. A power source in the oximeter system, such as an LED driver 182, is coupled to the tuned LED networks 164, 174 in order to provide a predetermined drive current at the input of the tuned LED networks 164, 174. Advantageously, the LED driver 182 provides current to only one of the tuned LED networks 164, 174 at any given time. The photodetector 180 is coupled to receiving and conditioning circuitry 184 in the oximeter system 152. In operation, the photodetector receives the attenuated light energy and responds with an output signal representing the intensity of the alternative light energy. The oximeter system 152 further comprises a controller 190 with supporting resources and a display 192. The oximeter system receives the signals obtained from the sensor 150 and analyzes the signals to determine information regarding the medium through which the light energy has been transmitted. It should be understood that the oximeter system is depicted in simplified form for discussion purposes. Oximeter systems are well known in the art. One possible oximeter system comprises the oximeter system disclosed in pending U.S. patent application Ser. No. 08/320,154 filed Oct. 7, 1994, which has been assigned to the assignee of the present application. Other oximeter systems are well known and can be designed to operate at the selected wavelengths.

Figure 4B:
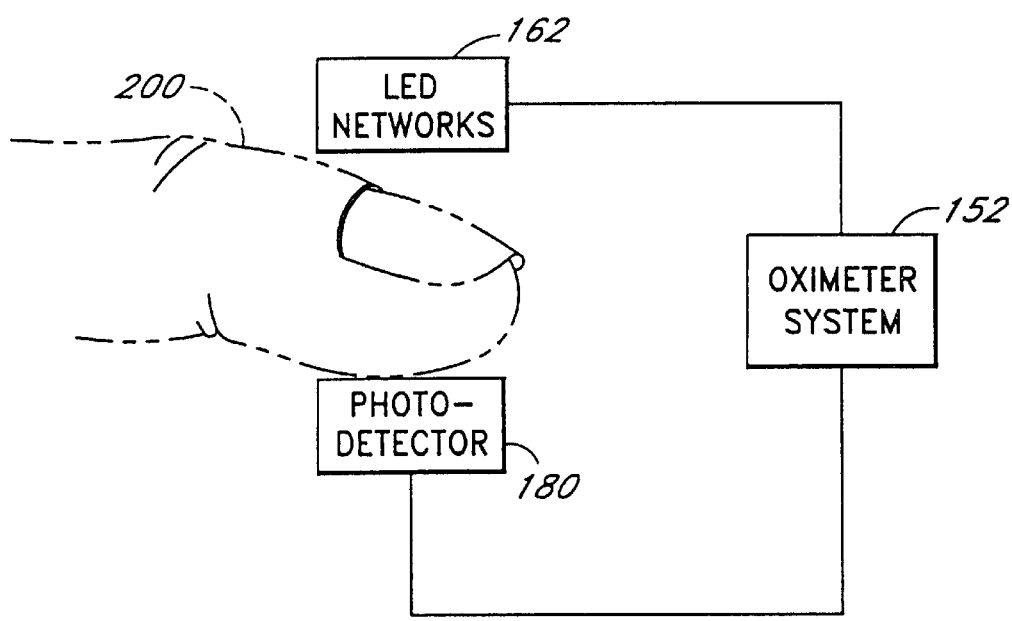
FIG. 4B depicts an oximeter system with a digit for monitoring.

As depicted in FIG. 4B, for oximetry, a typical medium may include a finger 200 or an earlobe, as well-known in the art. Media such as the finger and earlobe typically comprise a number of constituents such as skin, tissue, muscle, arterial blood and venous blood (having several constituents each), and fat. Each constituent absorbs and scatters light energy of a particular wavelength differently due to different extinction coefficients. In general operation, the first LED 162 emits incident light in response to the drive current from the LED driver 182. The light propagates through the medium under test. As the transmitted light propagates through the medium, it is partially absorbed by the medium. The attenuated light emerging from the medium is received by the photodetector 180. The photodetector 180 produces an electrical signal indicative of the intensity of the attenuated light energy incident on the photodetector 180. This signal is provided to the oximeter system 152, which analyzes the signal to determine the characteristics of a selected constituent of the medium through which the light energy has passed.

The tuning is now explained with reference to the first LED 160. The tuning is also applicable to the second LED 172. As explained above, in response to a particular drive current, different LEDs respond with different wavelengths, even though the LEDs were manufactured to generate the same wavelength. Tuning the first LED 160 in accordance with the present invention involves determining the amount of current required to operate the first LED 160 at the selected wavelength and adjusting the current through the first LED 160 in order to obtain the selected wavelength.

For instance, typical operational values for red LEDs used in oximetry range between 645 nm and 670 nm. For a particular embodiment of an oximeter, the oximeter may be designed to operate with a selected wavelength within that range, for example, 670 nm. However, the LEDs manufactured to produce the selected wavelength of 670 nm involve manufacturing tolerances typically in the range of ±2–10 nm for the same drive current. However, for a typical LED used in oximetry, the drive current can be varied in order to obtain the desired output wavelength for the LED. For instance, as illustrated in FIG. 3B, the represented LED has an operating wavelength of 660 nm for the typical 50 mA drive current. If the drive current is increased to approximately 85 mA, the operating wavelength becomes the selected wavelength of the present example (670 nm). The present invention takes advantage of the observed wavelength shift in response to a drive current change to tune each LED to obtain the selected wavelength, such as 670 nm.

For purposes of discussion, the first LED 160 is defined to exhibit the wavelength characteristic depicted in FIG. 3B. To tune the first LED 160, the drive current from the LED driver 182 is assumed to be preset or fixed. In the present embodiment, the drive current is preferably somewhat larger than the drive current necessary to drive the first LED 160 alone (e.g., 100 mA or more). This is because the first tuning resistor 162 carries some of the fixed drive current from the LED driver 182. The first tuning resistor 162 is selected to draw an appropriate amount of the fixed drive current to adjust the amount of current flowing through the first LED 160 to result in the selected output wavelength. In the present example, the resistor is chosen to carry approximately 15 mA (of the 100 mA from the LED driver 182) in order to reduce the current through the first LED 160 to approximately 85 mA to obtain the 670 nm selected wavelength. Accordingly, each LED can be driven with the same fixed drive current from the LED driver 182, yet the current through any particular LED differs in accordance with the value of the associated tuning resistor. In this manner, the LED driver 182 can be designed to provide the same fixed drive current for every sensor connected to the oximeter. The oximeter system 152 is thus designed to make its calculation based on the assumption that the corresponding wavelengths remain constant from sensor to sensor.

Figure 5A:
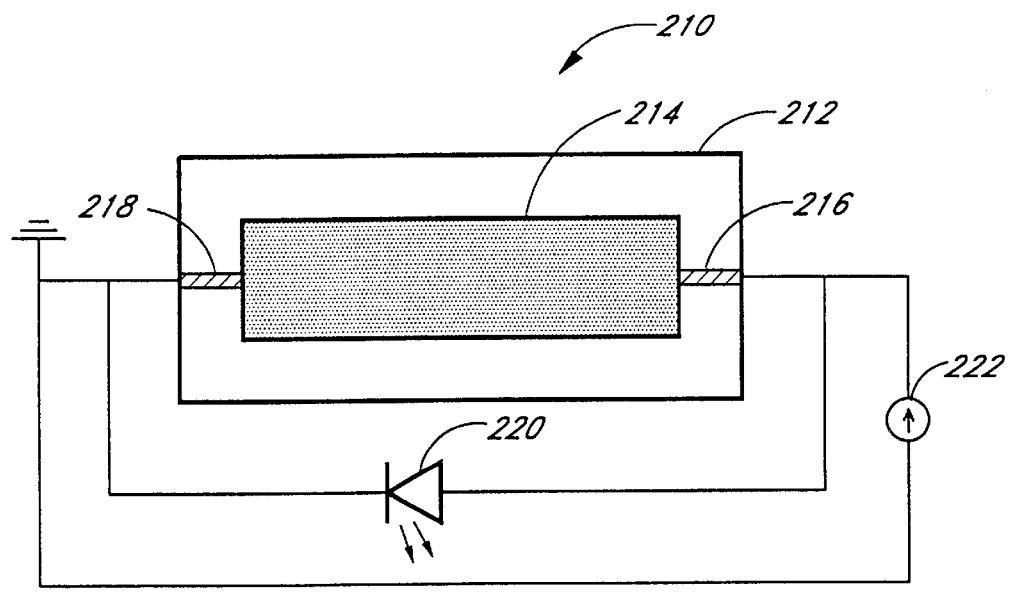
FIGS. 5A and 5B depict a representational diagram of one embodiment of a resistor for use in accordance with the present invention.
Figure 5B:
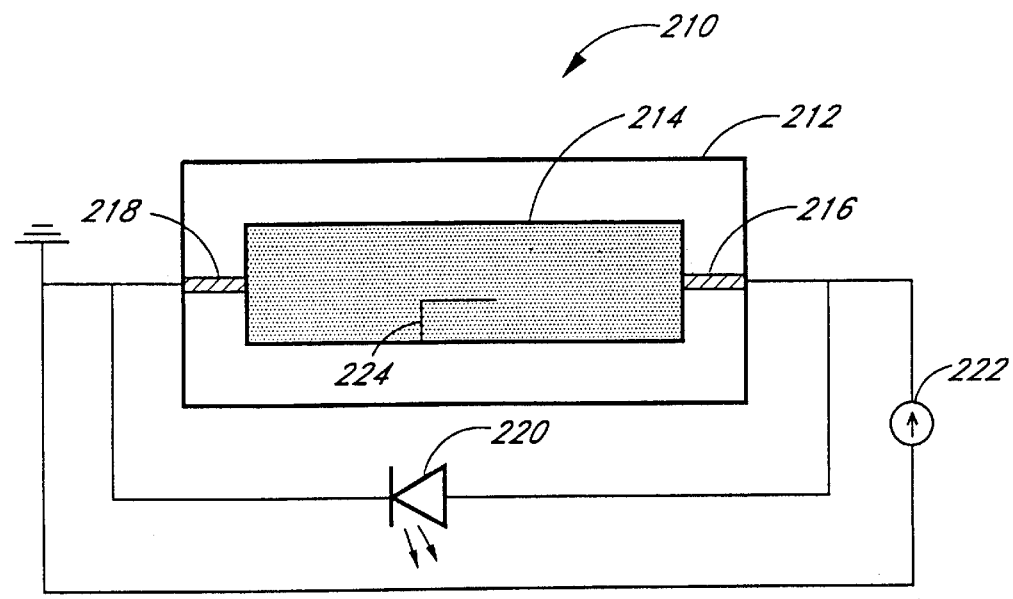

One particular advantageous method of selecting the tuning resistor involves the use of a semiconductor substrate resistor, such as the resistor 210 depicted in FIGS. 5A and 5B. The resistor 210 depicted in FIG. 5A comprises a semiconductor substrate 212, a resistive coating pad 214, and connective conductors 216, 218. In one embodiment a tunable LED 220 (i.e., an LED that exhibits wavelength shift with drive current change) is connected in parallel with the semiconductor substrate resistor 210. The fixed (preset) drive current is then applied with a current source 222 to the network formed by the substrate resistor 210 and the tunable LED 220. The operating wavelength of the tunable LED 220 is measured. Preferably, the initial substrate resistor has less resistance than will be necessary to obtain the desired output wavelength. A laser is used to scribe the resistive pad 214, as depicted by the line 224 in FIG. 5B. The scribe line 224 effectively removes a portion of the resistive pad 214, and thereby increases the resistance of the remaining resistive pad 214, as well known in the art. Using the laser, the increase in resistance can be controlled very precisely. The resistive pad 214 can be laser trimmed until the current through the tunable LED 220 causes the tunable LED 220 to generate the selected operating wavelength. The resulting resistor/LED pair forms a tuned LED network. This tuning method is advantageous because of the precision and the resulting low-cost of the tuned LED.

Other methods of selecting the first tuning resistor 162, such as calculating the wavelength shift for a given current change for the first LED 160, and then selecting the appropriate resistor to cause the correct amount of current to flow through the LED to obtain the selected operating wavelength, can also be used. Similarly, a potentiometer could be used. Preferably, each LED for each sensor is tuned in a similar manner such that the operating wavelength is a selected operating wavelength for the sensor. For instance, a two wavelength oximeter operating may have selected wavelengths for the two LEDs of 670 nm and 905 nm. For each sensor, a first LED is tuned for the 670 nm selected wavelength, and a second LED is tuned for the 905 nm selected wavelength.

In sum, the tuning aspect of the present invention involves using the principle of wavelength shift in an LED to tune each LED to obtain a respective selected operating wavelength.

Figure 6:
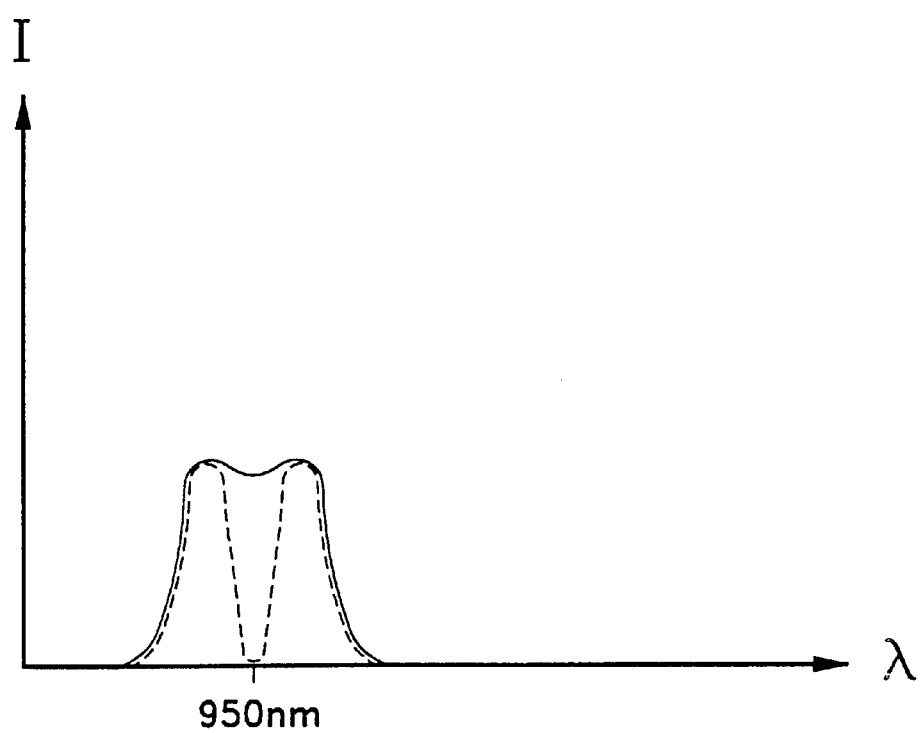
FIG. 6 depicts the averaging effect in the wavelength of two simultaneously active LEDs with close transmission wavelengths.

It should be understood that for some LEDs, the manufacturing tolerance may be too far from the respective selected wavelength to enable the use of the shift in wavelength to properly tune the LED; or the wavelength shift may be insufficient to obtain the selected wavelength. In one embodiment, such LEDs would not be utilized, and would be considered out of tolerance. Alternatively, if the obtainable wavelength shift is not sufficient to allow for proper tuning, it is also possible to use two LEDs having wavelengths very near each other and near the selected wavelength. One LED has a wavelength below the selected wavelength, and one LED has a wavelength above the selected wavelength. As the graph of FIG. 6 illustrates, when two LEDs are both active and placed adjacent one another, the light from the two LEDs combines to form a combined wavelength which is the average wavelength of the two LEDs. The combined wavelength has a broader wavelength range, but has a known average. Preferably, to fine tune the average wavelength, the wavelength shift of one or both of the two LEDs can be utilized using tuning resistors as described above such that the average wavelength is the selected wavelength. Accordingly, two LEDs (preferably tuned in accordance with the present invention as a pair) can be used to obtain the selected wavelength for operation in a given oximeter.

As another alternative, if sufficient wavelength shift is not available to allow for tuning all LEDs to the selected wavelengths, a few selected wavelengths could be used. For instance, for determining oxygen saturation, the selected red wavelengths could be 660 nm, 670 nm and 680 nm. The selected infrared wavelengths could be 900 nm, 920 nm, and 940 nm, independent of the red wavelengths. Each sensor would be tuned using the tuning resistors described above such that the red and infrared LEDs operate at one of the selected red and infrared wavelengths, respectively. An indicator would then be provided on the sensor, or the connector attached to the sensor, to allow the oximeter to determine which of the selected wavelengths is present on the sensor attached to the oximeter. Alternatively, a wavelength detection device could be provided with the oximeter system to determine which of the selected wavelengths is present in a sensor attached to the oximeter system. Although this embodiment requires some means for the oximeter to determine which of the selected wavelengths is present on the attached sensor, the selected wavelengths are precise from sensor to sensor.

Two-Wavelength LED

Another aspect of the present invention involves using the principle of wavelength shift in an LED for a given change in current in order to use a single LED to provide two operating wavelengths. This is advantageous in making physiological measurements, such as blood oximetry measurements, because for each additional wavelength added, the saturation of an additional constituent in the blood can be measured. For instance, with a two-wavelength oximeter, only the ratio of one of two constituents to the total of the two constituents (e.g., oxygen saturation) can be accurately monitored. If oxygen saturation is monitored with two wavelengths, other constituents which are significantly present in the blood affect the measurement of oxygen saturation.

If an additional constituent present in the blood has a significant effect upon the oxygen saturation reading for a particular patient, the failure to detect the constituent can be detrimental to the patient. An example of a constituent which, when present in the blood, will significantly impact the oxygen saturation reading provided by a two-wavelength oximeter is carbon monoxide. This is because the extinction coefficient magnitude for carboxyhemoglobin (depicted in the curve 106 of FIG. 2) approaches the extinction coefficient of oxyhemoglobin (depicted in the curve 102 of FIG.

2) for light energy in the range of 660 nm. Therefore, carboxyhemoglobin may be detected as oxyhemoglobin. This leads to a false indication of the oxygen saturation (i.e., overestimation) in the blood using a two-wavelength oximeter. In this manner, the attending physician may fail to detect the lack of oxygen, and the increase of carbon monoxide in a patient. If an additional transmission wavelength is provided on the sensor, the oximeter can monitor another constituent, such as carboxyhemoglobin.

In accordance with the present invention, the principle of wavelength shift in an LED is utilized in order to drive one LED with two appropriate drive current levels to provide two distinct wavelengths. In its simplest form, this is accomplished by first driving an LED (which exhibits wavelength shift with drive current change) with a first known drive current to a first known wavelength, and then driving the same LED with a second known current to a second known wavelength.

Figure 7:
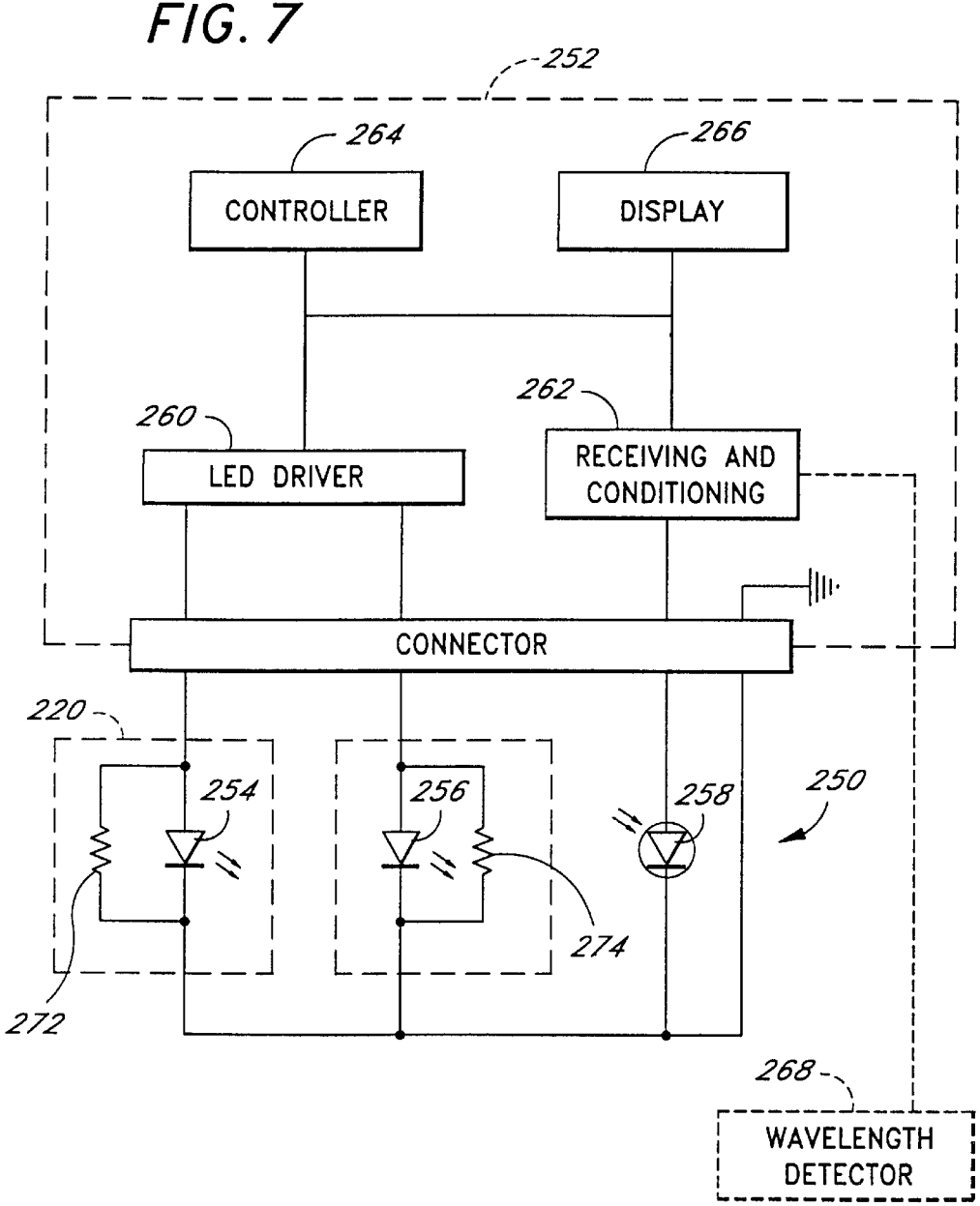
FIG. 7 depicts an embodiment of an oximeter sensor according to another aspect of the present invention.

FIG. 7 depicts one advantageous embodiment of a sensor 250 for blood oximetry measurements coupled to an oximeter system 252 designed in accordance with this aspect of the present invention. The sensor 250 comprises a first LED 254 and a second LED 256. For blood oximetry the first LED 254 preferably operates in the red wavelength range and the second LED 256 preferably operates in the infrared wavelength range. The sensor 250 further comprises a photodetector 258. The photodetector 258 is coupled to receiving and conditioning circuitry 262. The oximeter system is under the control of a controller 264 and has a display 266. As well-understood in the art, an LED driver 260 sequentially drives the LEDs 254, 256 with a predetermined drive current. The photodetector 258 detects the light energy, attenuated by the medium under test. The oximeter 252 receives and analyzes the signal from the photodetector 258 to determine information regarding the medium through which the light energy has been transmitted. As with the embodiment of FIG. 4, the oximeter system 252 is depicted in simplified form. Appropriate oximeter systems include the system disclosed in copending U.S. patent application Ser. No. 08/320,154, filed Oct. 7, 1994, which has been assigned to the assignee of the present application. Other monitors well understood in the art also exist. The oximeter system 252 is modified in accordance with the present invention to drive the shifting LED as described below.

In the present example for blood oximetry, the first LED 254 is the shifting LED and is used to provide two wavelengths. In order to accurately provide two wavelengths, the wavelength shift principle is utilized. According to one embodiment, LEDs are evaluated at the time a sensor is manufactured, and an indicator is provided on the sensor which can be read by the oximeter system 252 to indicate the drive current change necessary in order to effectuate a desired shift in wavelength. Indicators may comprise a resistor on the sensor or sensor connector, a memory on the sensor or sensor connector, or a similar device. Alternatively, the indicator can provide a indication to the oximeter of the amount of wavelength shift which is obtained due to a preset drive current change. Another alternative is to provide a wavelength detector 268 for the oximeter, which allows the oximeter system 252 to detect the transmission wavelength of an active LED. Wavelength detectors, such as a monochromer, are well known in the art. However, conventional monochrometers are expensive and bulky. This description sets forth a more practical approach to detecting wavelength below. In this embodiment, the LED driver 260 changes the drive current until the desired wavelength is obtained, utilizing the wavelength detector 268 to monitor the wavelength.

In one preferred embodiment allowing for a simpler oximeter design, in order to accurately provide two wavelengths with a single LED such as the first LED 254, a network 270 of a slope adjusting resistor 272 and the first LED 254 is slope adjusted such that a preselected change in drive current ($\Delta I$) entering the first slope adjusted network, causes a preselected shift in wavelength ($\Delta\lambda$) in the first LED 254. In other words, as depicted in FIG. 3B, each LED exhibits an inherent slope of the curve 122. However, the slope of this curve often differs from LED to LED, even for LEDs rated for a particular wavelength. In order for an oximeter to be designed for simplicity in obtaining a repeatable preselected wavelength shift, it is advantageous to have the preselected wavelength shift ($\Delta\lambda$) for each first LED in different sensors correspond to the same preselected drive current change ($\Delta I$). Accordingly, it is desirous that the first LED (for the present example) on different probes respond with the same preselected change in wavelength for the same change in drive current provided by the LED driver 260. In other words, it is advantageous that the slope of the curve 100 depicted in FIG. 3B be the same for each corresponding LED network, since it is not typically the same for each individual LED. In this manner, the oximeter is designed to drive the LEDs with two drive current levels, where the two drive current levels are preselected and remain constant from sensor to sensor.

Just as the first tuning resistor 162 tunes the first LED 160 to a particular selected wavelength for a selected drive current, a slope adjusting resistor, such as the slope adjusting resistor 272, can be used to alter the slope of the curve 122 exhibited for the particular corresponding LED network (e.g., the first slope adjusted LED network 270). In most instances, the slope adjusting resistor 272, if used to alter the slope, cannot also be used to tune the precise wavelength of the first LED 254. However, other methods and procedures to indicate to the oximeter what the particular wavelength of operation of the first LED for a given drive current can be utilized. For instance, an indicator (such as a resistor or low cost memory device) can be provided with the sensor 250 which can be read by the oximeter 252, which indicator provides the initial operating wavelength of the slope adjusted LED network 270.

Slope adjustment can be accomplished in the same manner as described above with respect to the semiconductor substrate resistor 210. However, the substrate resistor functions as the slope adjusting resistor rather than a wavelength tuning resistor (i.e., the substrate resistor is adjusted to cause a preselected change in wavelength for a preselected change in drive current for the LED/resistor network). In other words, for the first LED 254, the substrate resistor 210 depicted in FIGS. 5A and 5B is coupled to the first LED 254 to form the slope adjusting resistor 272. A laser is used to trim the resistor until the preselected change in drive current for the network 270 results in the preselected change in wavelength for the first LED 254.

It should be noted that if LEDs are available that exhibit the same wavelength shift with respect to the same change in drive current, the first slope adjusting resistor 272 is unnecessary.

For determining oxygen saturation, the second LED 256 operates at a fixed infrared wavelength (e.g., 905 nm). Preferably, if the infrared LEDs exhibit manufacturing tolerances, the infrared LEDs can be tuned using a tuning resistor 274, in the same manner as the tuning resistor 162 of FIG. 4, to operate at the selected infrared wavelength. With a tuned second (infrared) LED 256 and a slope adjusted first LED 254 (configured to provide two wavelengths), measurements at three wavelengths can be taken using the sensor 250.

In use, the sensor 250 of FIG. 7 is first driven with an initial drive current to cause the first LED 254 to generate light energy of a first wavelength (e.g., 660 nm). The attenuated signal at this first wavelength is detected by the photodetector 258 and received by the oximeter 252. Next, the first slope adjusted LED 254 is driven with a new drive current varied by the preselected change in drive current to cause the preselected wavelength shift to obtain a second wavelength (e.g., 675). As long as the initial wavelength is provided to the oximeter system 252, and the slope (change in wavelength due to change in current) of the first LED network 270 is properly adjusted to match the preselected slope, the second wavelength will also be a known quantity. A third measurement is taken by driving the second LED 256 and receiving the attenuated signal with the photodetector 258. Measurements are stored in the oximeter system 252. Based upon the three measurements taken, the arterial saturation of two constituents of blood may be determined (e.g., oxyhemoglobin and carboxyhemoglobin), thus providing more precise information regarding the physiological makeup of the blood of a patient under test.

In an oximeter system where monitoring of carbon monoxide and oxygen is desired, the first wavelength may be 660 nm, the second wavelength may be 675 nm or 680 nm and the third wavelength will be an infrared wavelength such as 900 nm or 905 nm. With these three wavelengths provided by two LEDs, the saturation of both oxyhemoglobin and carboxyhemoglobin in blood can be determined. The use of two LEDs to perform measurements at three wavelengths reduces the cost of the sensor, which is particularly advantageous if the sensor is a disposable or replaceable sensor.

In addition to the uses described above, it should also be noted that the wavelength shift principal described above could be used to obtain an additional wavelength with one LED for use in the ratiometric method of determining blood oxygen as described in copending U.S. patent application Ser. No. 07/672,890, filed Nov. 21, 1991, which has been assigned to the assignee of the present application.

Measurements Without Precise Wavelength Information

A further aspect of the present invention involves an apparatus and method of measuring the saturation of a selected constituent in a medium under test (e.g., oxyhemoglobin in blood) without knowing the precise operational wavelength of one LED. According to this aspect of the present invention, if the wavelength shift for an LED is known for a known change in drive current, the operational wavelength for the LED need not be known if other information is also available, as further explained below.

As explained above, obtaining a known wavelength shift for a selected change in current can be accomplished by adjusting presently existing LEDs, such that the LEDs react to a preselected change in drive current ($\Delta I$) with a preselected change in wavelength ($\Delta\lambda$). Alternatively, if LEDs are available having a repeatable (from LED to LED) change in wavelength for a selected change in current, those LEDs can be used without adjustment. An understanding of this aspect of the present invention is explained with reference to arterial oxygen saturation determination using two-wavelength oximeters.

As explained above, FIG. 2 depicts a graph illustrating the relationship between the typical extinction coefficient for three constituents of blood with respect to the transmission wavelength of light transmitted through the blood. For purposes of determining oxygen saturation, the first curve 102 and second curve 104 are of interest.

As illustrated by the first curve 102, the extinction coefficient of oxyhemoglobin for light transmitted between approximately 665 nm (indicated as $\lambda_1$ on the graph) and 690 nm (indicated as $\lambda_2$ on the graph) is substantially constant (more apparent when the Y-axis of FIG. 2 is not a log scale axis). When light within that same range (i.e., $\lambda_1$–$\lambda_2$) is transmitted through reduced hemoglobin (the second curve 104), the extinction coefficient of the reduced hemoglobin exhibits a substantially linear relationship as a function of transmission wavelength. These known properties of blood constituents are utilized in the apparatus and method of the present invention to obtain information regarding the oxygen saturation (or other constituent saturation) of the blood without knowing the particular wavelength of one of two LEDs.

Assuming that incident light is represented by the letter $I_o$ and the attenuated signal is represented by I, the attenuated signal is represented by Equation (1) above. In other words, for the LED sensor 250 of FIG. 7, the attenuated signal I is received by the photodetector 258 and is a function of the ambient transmission, as set forth in Equation (1).

Where light of wavelength $\lambda$ is transmitted through tissue with blood containing two forms of hemoglobin (oxyhemoglobin and reduced hemoglobin), Equation (1) can be expanded for these two constituents of blood:

$$I = I_o\left(e^{-\sum_{j=1}^a \varepsilon_j d_j c_j}\right)(e^{-d\varepsilon_{1\lambda}c_1})(e^{-d\varepsilon_{2\lambda}c_2}) \qquad (2)$$

where:

d is the thickness of the medium.

$\varepsilon_{1\lambda}$ is the absorption coefficient of reduced hemoglobin at wavelength $\lambda$, $\varepsilon_{2\lambda}$ is the absorption coefficient of oxyhemoglobin at wavelength $\lambda$, $c_1$ is the concentration of reduced hemoglobin, $c_2$ is the concentration of oxyhemoglobin, $\varepsilon_j$ is the absorption coefficient of the $j^{th}$ layer of attenuating material (not including oxyhemoglobin and reduced hemoglobin), $d_j$ is the thickness of the $j^{th}$ layer of attenuation material (not including oxyhemoglobin and reduced hemoglobin), and $c_j$ is the concentration of the $j^{th}$ layer of attenuating material (not including oxyhemoglobin and reduced hemoglobin).

Equation (2) can be further expressed as follows:

$$S = \ln\left(\frac{I}{I_{BL}}\right) = -d(\varepsilon_{1\lambda}c_1 + \varepsilon_{2\lambda}c_2) \qquad (3)$$

where:

$$I_{BL} = I_o\left(e^{-\sum_{j=1}^a \varepsilon_j d_j c_j}\right) = \text{baseline}$$

s is a value obtained by measuring I with the photodetector and calculating the ratio of I to $I_{BL}$ after taking the natural log.

For determining oxygen saturation, where the light is transmitted at a first red wavelength $\lambda_1$, Equation (3) is expressed as follows:

$$S_1 = \ln\left(\frac{I}{I_{BL}}\right)\Big|_{\lambda_1} = -d(\varepsilon_{1\lambda_1} c_1 + \varepsilon_{2\lambda_1} c_2) \qquad (4)$$

Where light is transmitted at an infrared wavelength $\lambda_{IR}$, Equation (3) is expressed as follows:

$$\left(S_{IR} = \ln\left(\frac{I}{I_{BL}}\right)\right)\Big|_{\lambda_{IR}} = -d(\varepsilon_{1\lambda_{IR}} c_1 + \varepsilon_{2\lambda_{IR}} c_2) \qquad (5)$$

When the wavelength $\lambda_1$ and the wavelength $\lambda_{IR}$ are both known, the oxygen saturation can be determined, as well-understood in the art. This is briefly illustrated with the following derivation:

$$\text{LET } N_1 = \frac{S_1}{d} \text{ and } N_2 = \frac{S_{IR}}{d} \qquad (6)$$

Equations (4) and (5) become:

$$N_1 = C_2 \varepsilon_{2\lambda_1} + C_1 \varepsilon_{1\lambda_1} \qquad (7)$$

$$N_2 = C_2 \varepsilon_{2\lambda_{IR}} + C_1 \varepsilon_{1\lambda_{IR}} \qquad (8)$$

In matrix notation, Equations (7) and (8) become:

$$A = \begin{pmatrix} \varepsilon_{2\lambda_1} & \varepsilon_{1\lambda_1} \\ \varepsilon_{2\lambda_{IR}} & \varepsilon_{1\lambda_{IR}} \end{pmatrix} \quad X = \begin{pmatrix} C_2 \\ C_1 \end{pmatrix} \quad B = \begin{pmatrix} N_1 \\ N_2 \end{pmatrix}$$

$$A \cdot X = B \Rightarrow \begin{pmatrix} \varepsilon_{2\lambda_1} & \varepsilon_{1\lambda_1} \\ \varepsilon_{2\lambda_{IR}} & \varepsilon_{1\lambda_{IR}} \end{pmatrix} \begin{pmatrix} C_2 \\ C_1 \end{pmatrix} = \begin{pmatrix} N_1 \\ N_2 \end{pmatrix} \qquad (9)$$

$$\text{Or}: \begin{pmatrix} C_2 \\ C_1 \end{pmatrix} = \begin{pmatrix} \varepsilon_{2\lambda_1} & \varepsilon_{1\lambda_1} \\ \varepsilon_{2\lambda_{IR}} & \varepsilon_{1\lambda_{IR}} \end{pmatrix}^{-1} \begin{pmatrix} N_1 \\ N_2 \end{pmatrix}$$

$$\text{Hence}: \begin{pmatrix} C_2 \\ C_1 \end{pmatrix} = \begin{bmatrix} \frac{(\varepsilon_{1\lambda_{IR}} N_1 - \varepsilon_{1\lambda_1} N_2)}{(\varepsilon_{2\lambda_1} \varepsilon_{1\lambda_{IR}} - \varepsilon_{1\lambda_1} \varepsilon_{2\lambda_{IR}})} \\ \frac{(-\varepsilon_{2\lambda_1} N_1 + \varepsilon_{2\lambda_1} N_2)}{(\varepsilon_{2\lambda_1} \varepsilon_{1\lambda_{IR}} - \varepsilon_{1\lambda_1} \varepsilon_{2\lambda_{IR}})} \end{bmatrix} \qquad (10)$$

As well understood in the art, oxygen saturation is defined as the following ratio:

$$\text{oxygen}: SAT = \frac{C_2}{C_2 + C_1} \Rightarrow \frac{1}{SAT} = \frac{C_2 + C_1}{C_2} \qquad (11)$$

$$\text{Or}: \frac{1}{SAT} = 1 + \frac{C_1}{C_2}$$

$$\text{Hence}: \frac{C_1}{C_2} = \frac{\frac{(-\varepsilon_{2\lambda_1} N_1 + \varepsilon_{2\lambda_1} N_2)}{(\varepsilon_{2\lambda_1} \varepsilon_{1\lambda_{IR}} - \varepsilon_{1\lambda_1} \varepsilon_{2\lambda_{IR}})}}{\frac{(\varepsilon_{1\lambda_{IR}} N_1 - \varepsilon_{1\lambda_1} N_2)}{(\varepsilon_{2\lambda_1} \varepsilon_{1\lambda_{IR}} - \varepsilon_{1\lambda_1} \varepsilon_{2\lambda_{IR}})}}$$

$$\text{Substituting}: N_1 = \frac{S_1}{d} \text{ and } N_2 = \frac{S_{IR}}{d}$$

and multiplying the numerator and denominator by $-1$:

$$\text{and Simplifying}: \frac{C_1}{C_2} = \frac{\varepsilon_{2\lambda_1}\left(\frac{S_1}{d} - \frac{S_{IR}}{d}\right)}{\left(-\varepsilon_{1\lambda_{IR}} \frac{S_1}{d} + \varepsilon_{1\lambda_1} \frac{S_{IR}}{d}\right)}$$

Multiplying numerator and denominator by d:

$$\frac{C_1}{C_2} = \frac{\varepsilon_{2\lambda_1}(S_1 - S_{IR})}{(-\varepsilon_{1\lambda_{IR}} S_1 + \varepsilon_{1\lambda_1} S_{IR})} \qquad (12)$$

Substituting Equation (12) into Equation (11) above:

$$\frac{1}{SAT} = \frac{\varepsilon_{2\lambda_1}(S_1 - S_{IR})}{(-\varepsilon_{1\lambda_{IR}} S_1 + \varepsilon_{1\lambda_1} S_{IR})} + 1$$

Simplifying:

$$\frac{1}{SAT} = \frac{(\varepsilon_{2\lambda_1} S_1 - \varepsilon_{2\lambda_1} S_2 - \varepsilon_{1\lambda_{IR}} S_1 + \varepsilon_{1\lambda_1} S_2)}{-\varepsilon_{1\lambda_{IR}} S_1 + \varepsilon_{1\lambda_1} S_2)}$$

AND FINALLY:

$$SAT = \frac{(\varepsilon_{1\lambda_{IR}} S_1 + \varepsilon_{1\lambda_1} S_2)}{(-\varepsilon_{2\lambda_1} S_1 + \varepsilon_{2\lambda_1} S_2 + \varepsilon_{1\lambda_{IR}} S_1 - \varepsilon_{1\lambda_1} S_2)} \qquad (13)$$

When the wavelength $\lambda_1$ and the $\lambda_{IR}$ are both known, the extinction coefficients, $\epsilon_{1\lambda_1}$, $\epsilon_{2\lambda_1}$, $\epsilon_{1\lambda_{IR}}$ and $\epsilon_{2\lambda_{IR}}$, for the corresponding constituents at $\lambda_1$, and $\lambda_{IR}$ are also known. As explained above, $S_1$ and $S_{IR}$ can be obtained by measuring I and $I_o$ and taking the natural log of this ratio at the various wavelengths during operation. Accordingly, all of the variables in the saturation equation are known or obtainable through measurement.

However, if the wavelengths for the transmission LEDs are not specifically known, the extinction coefficients $\epsilon$ will not be known. In accordance with one aspect of the present invention, the oxygen saturation can be computed without knowing the precise wavelength of one of the LEDs. For purposes of discussion herein, the LED in the red range is chosen for illustration of this aspect of the present invention. In accordance with the present invention, and as explained above, the red LED can be adjusted to exhibit a preselected wavelength shift, even though the precise wavelength may not be known. Accordingly, the red LED can be driven with two different drive currents to obtain two different wavelengths, the shift between which is preselected and known. However, as explained above, the precise wavelength may be unknown without some indication of at least the starting wavelength. In accordance with the present invention, as long as the preselected wavelength shift is known, the starting wavelength need not be known.

In an application where the extinction coefficients vary with respect to shifts in wavelength on the order of 1–3 nm, it would be possible to determine the wavelength without prior information regarding the wavelength or the wavelength shift. This would be accomplished by calculating the desired measurement (e.g., oxygen saturation) at several (e.g., two or more) different LED drive currents and using the change in the measurement in connection with an empirically generated data set (i.e., curves) of measurements with respect to wavelengths to determine the wavelength of the LED.

If the preselected wavelength shift is utilized, the oximeter system can make measurements at three wavelengths $\lambda_1$, $\lambda_2$ and $\lambda_{IR}$. Thus, a third equation in addition to Equations (3) and (4) is obtained.

Where the light is transmitted at a second red wavelength $\lambda_2$, Equation (3) is expressed as follows:

$$S_2 = \ln\left(\frac{I}{I_{BL}}\right)\bigg|_{\lambda_2} = -d(\varepsilon_{1\lambda_2}c_1 + \varepsilon_{2\lambda_2}c_2) \quad (14)$$

As depicted in FIG. 2, within the range of 650 nm–700 nm, the extinction coefficient does not significantly change. More particularly, within the range of $\lambda_1$–$\lambda_2$=665 mm–690 mm, $$\varepsilon_{2\lambda_2} \cong \varepsilon_{2\lambda_1} \quad (15)$$

Furthermore within the same range, $$\varepsilon_{1\lambda_2} = (\varepsilon_{1\lambda_1} - \Delta\varepsilon_1) \quad (16)$$

$\Delta\varepsilon_1$ is known for a known wavelength shift within the described range, because the change in the extinction coefficient $\Delta\varepsilon_1$ is substantially linear.

Substituting Equations (14) and (15) into Equation (4), (5), and (14) results in the following equations:

$$S_1 = -d(\varepsilon_{1\lambda_1}c_1 + \varepsilon_{2\lambda_2}c_2) \quad (17)$$

$$S_{IR} = -d(\varepsilon_{1\lambda_{IR}}c_1 + \varepsilon_{2\lambda_{IR}}c_2) \quad (18)$$

$$S_2 = -d((\varepsilon_{1\lambda_1} - \Delta\varepsilon_1)c_1 + \varepsilon_{2\lambda_2}c_2) \quad (19)$$

As explained above, $S_1$, $S_2$, and $S_{IR}$ are calculated by measuring I and $I_{BL}$. Accordingly, $S_1$, $S_2$, and $S_{IR}$, are known values. The extinction coefficients $\varepsilon_1$ and $\varepsilon_2$ for the infrared wavelength LED are assumed to be known because in the infrared wavelength of interest (e.g., 850 mn–920 nm) and more particularly 890 nm–910 nm), the extinction coefficient is substantially constant for both curves 102 and 104. In another embodiment, the accuracy would be improved slightly by tuning the LED. The extinction coefficients for oxyhemoglobin at $\lambda_1$ and $\lambda_2$ are also known, as long as the wavelength is in the range where the extinction coefficient remains constant. In the present example, this range is defined as 665 nm to 690 nm. Furthermore, because the change in the absorption coefficient ($\Delta\varepsilon_1$) for reduced hemoglobin is known for a known wavelength shift between $\lambda_1$–$\lambda_2$=665 nm–690 nm, $\Delta\varepsilon_1$ is also a known quantity because $\varepsilon_1$ is linear with $\lambda$. The total thickness of the medium, d, generally is unknown for most applications. However, for the determination of oxygen saturation, as illustrated above, the thickness (d) cancels because saturation is a ratio.

Accordingly, for the determination of oxygen saturation, Equations (17), (18), and (19) provide three equations with three unknowns ($\varepsilon_{1\lambda_1}$, $c_1$ and $c_2$). Algebraic techniques following those of Equations (6) to (13) may be applied to solve the three equations to obtain the oxygen saturation ratio of $c_2/(c_1+c_2)$. Accordingly, it is not necessary to know the precise operating wavelength of the first LED 254, as long as the operating wavelength for the first LED 254 is in a known range where a preselected change in drive current causes a preselected change in the wavelength, and where the extinction coefficient of one constituent is constant and the extinction coefficient of the second constituent is substantially linear such that the change in the extinction coefficient for a preselected change in wavelength is also known.

Accordingly, this aspect of the present invention permits the user to obtain physiological data without knowing the precise operational frequency of an LED.

Improved Calibration of LED Sensor

Figure 1:
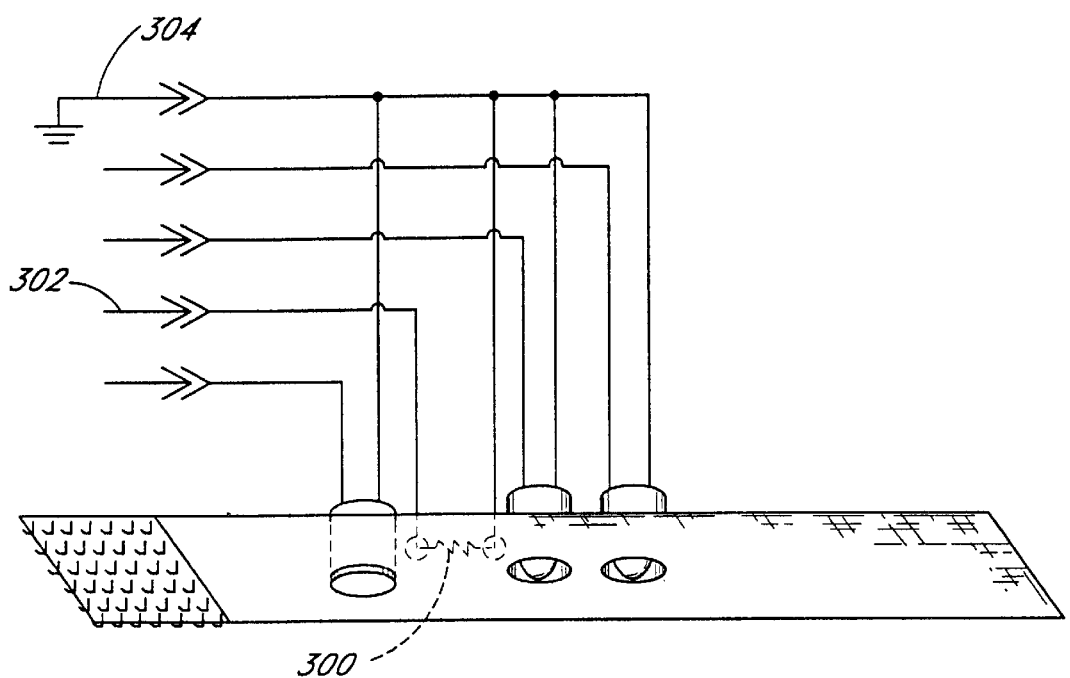
FIG. 1 represents a calibrated prior art oximeter probe.

An additional aspect of the present invention involves an improved calibration technique for an oximeter sensor where a resistor is utilized to code the LED rather than tune the LED. As depicted in the prior art calibrated oximeter probe of FIG. 1, an encoding resistor 300 utilizes a separate electrical connection lead and connects to a common ground lead 304. With the ever increasing use of replaceable or disposable sensors, any reduction in the complexity of the replaceable sensor can result in a significant cost savings over time. In accordance with present invention, the characteristics of an LED as depicted in FIG. 3A can be utilized to provide a more cost effective coded or calibrated oximeter probe where the coding or calibration is provided using a coding resistor.

Figure 8:
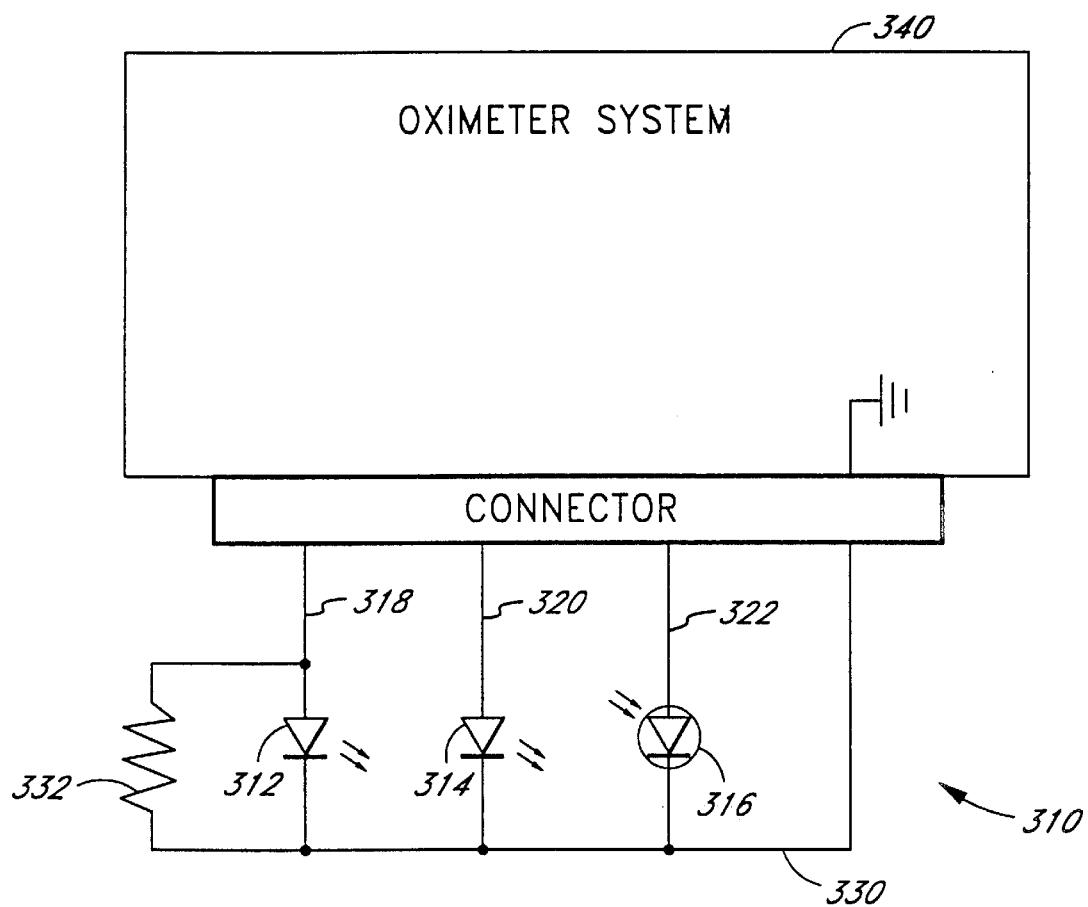
FIGS. 8 and 8A depict exemplary embodiments of improved calibrated oximeter sensors.

In accordance with this aspect of the present invention, one of the LED electrical connections can also be used for the coding resistor. FIG. 8 depicts a schematic diagram of an exemplary oximeter sensor where a coding resistor 332 can be read using one of the LED electrical connections rather than a separate electrical connection. A sensor 310 comprises a first LED 312, a second LED 314 and a photodetector 316. The first LED 312 has a first corresponding electrical connection 318; the second LED 314 has a second corresponding electrical connection 320; and the photodetector 316 has a corresponding electrical connection 322. Each of the LEDs 312, 314 and the photodetector 316 are connected at their outputs to a common ground electrical connection 330. In the present embodiment, the coding resistor 332 is coupled in parallel with the first LED 312 or the second LED 314. In this embodiment, the coding resistor 332 is not provided to tune the first LED 312 or to slope adjust the first LED network, but is provided as an indicator which can be read by an attached oximeter system 340. The resistor can be used to indicate the operating wavelength of the first and second LEDs 312, 314, or more advantageously, to indicate the type of probe. In other words, the value of the coding resistor 332 can be selected to indicate that the probe is an adult probe, a pediatric probe, a neonatal probe, a disposable probe or a reusable probe. In one preferred embodiment, coding resistors could be provided across each of the LEDs 312, 314 to allow additional information about the probe to be coded without added leads. However, any resistor or impedance device could be used without it being used in parallel with the LEDs to encode the change in wavelength or other information for the LEDs.

For instance, the coding resistor could be utilized for security purposes. In other words, the value of the coding resistor, and the placement across the LED 312 could be used to ensure that the probe is configured properly for the oximeter. For instance, the coding resistor could be utilized to indicate that the probe is from an authorized supplier such as a "Masimo" standard probe, "Patient Monitoring Company 1" probe, "Patient Monitoring Company 2" probe, etc.

In addition, it should be noted that the resistor need not be a passive element. Coding information could also be provided through an active circuit such as a transistor network, memory chip, or other identification device, for instance Dallas Semiconductor DS 1990 or DS 2401 or other automatic identification chip.

In order to read the coding resistor 332, the oximeter system 340 drives the first LED 312/coding resistor 332 combination at a level that is low enough that the LED draws effectively insignificant current because of the exponential relationship between I and V, as illustrated in the graph of FIG. 3A. As well understood in the art, the LED becomes active in the area of the shoulder, designated with the A axis indicator. Below the voltage level at A, the LED is effectively inactive and draws effectively insignificant current. In other words, the current through the first LED 312 is negligible. Significantly all of the current through the first electrical connection 318 flows through the coding resistor 332.

The current which flows through the coding resistor for the voltage applied is measured by the oximeter system by measuring the current through the first electrical connection 318. In turn, the oximeter system 340 determines the value of the coding resistor 332 which is preselected to indicate the type of probe, the operating wavelength or other parameters about the probe. In essence, by reducing the drive voltage across the first electrical connection 318 and ground to a low level that does not activate the first LED 312, the first LED 312 is effectively removed from the electrical circuit. In the present embodiment, it has been found that for conventional LEDs in the red and IR range, 0.5V is a particularly advantageous voltage. At 0.5V, current through the LED is generally less than 1 μA (an insignificant amount).

Preferably, the coding resistor 332 is chosen to be of a sufficiently high value that when the current supply to the first electrical connection 318 rises to a level sufficient to drive the first LED 312, the coding resistor 332 is effectively removed from the electrical circuit because of its high resistance as compared to the resistance of the first LED 312 at active operating currents.

Accordingly, a coding resistor can be used in connection with an oximeter LED sensor without the addition of an electrical connector dedicated to the coding resistor. This reduces the cost of the sensor in accordance with the present invention.

In one advantageous embodiment, the oximeter can monitor the coding resistor continuously by providing a 0.5V coding resistor reading signal at a frequency different from the LED drive current. For instance, if the LED drive current is turned on and off at a frequency of 625 Hz, the 0.5V coding resistor reading voltage can be provided at a frequency much lower than 625 Hz, such that the 625 Hz signal can be easily filtered with a low pass filter with a cutoff significantly below 625 Hz, but with a pass band which allows the 0.5V signal to pass. This would allow the oximeter to continuously monitor the coding resistor 332 in case of a change in the sensor by the system operator.

Figure 8A:
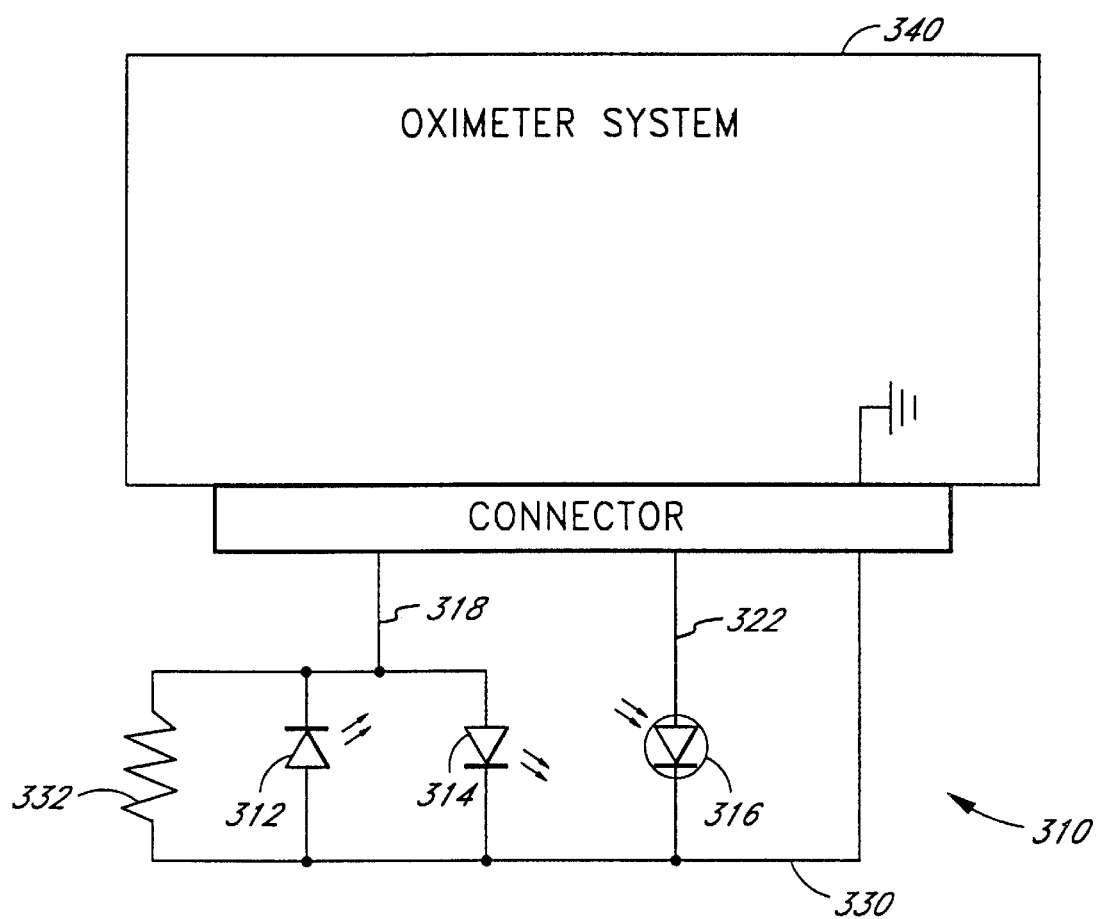

This particularly advantageous embodiment of using the coding resistor 332 can also be utilized with a conventional back-to-back configuration for the red and infrared LEDs, as is typical in oximeters. Such a configuration is depicted in FIG. 8A. FIG. 8A is similar to FIG. 8, except that the first LED 312 and the second LED 314 are connected in a back-to-back configuration such that the first electrical connection 318 is required and the voltage can be alternated from positive to negative to draw current through either the second LED 314 or the first LED 312. This eliminates the need for an electrical connection to the oximeter probe, thereby further reducing the cost of the probe. In the back-to-back configuration of FIG. 8A, if the second LED 314 is a red LED with a knee of approximately 2.0V and that the second LED 312 is an infrared (IR) LED with a knee of approximately 1.5V, a positive voltage is advantageously applied to the first electrical connection 318 at approximately 0.5V in order to measure the coding resistor 332. Because the knee for the red LED is 2.0V, very little (less than 1 μA) current will flow through the red LED and essentially no current will flow through the infrared LED 312 (because the infrared LED 312 is reverse biased). In such a scenario, the current which passes through the network of the first LED 312, the second LED 314, and the coding resistor 332 is approximately equal to the current through the coding resistor 332. The resistance of the coding resistor 332 is then easily determined via Ohms Law by dividing the voltage applied to the network by the current which flows through the network. Care must be taken to insure that the element (active or passive) does not create electromagnetic noise which could lead to reduced system signal to noise ratio.

Wavelength Detection

Figure 9A:
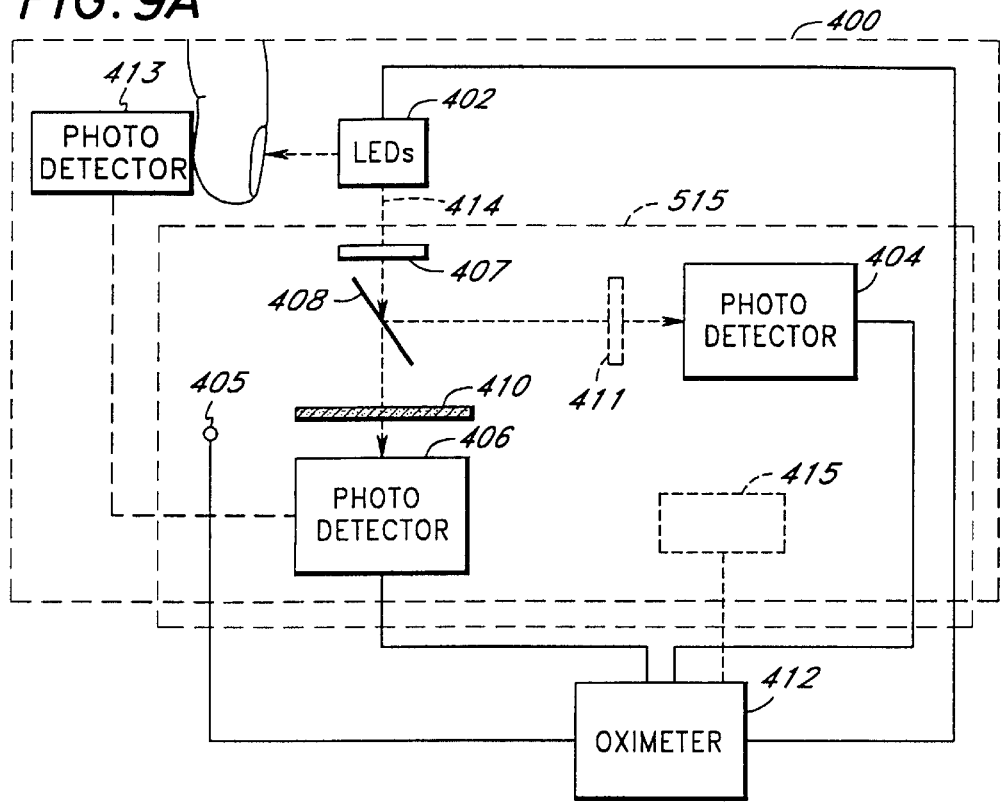
FIGS. 9A and 9B depict alternative embodiments sensors in accordance with of one aspect of the present invention relating to detecting the wavelength of light emitting diodes.
Figure 9B:
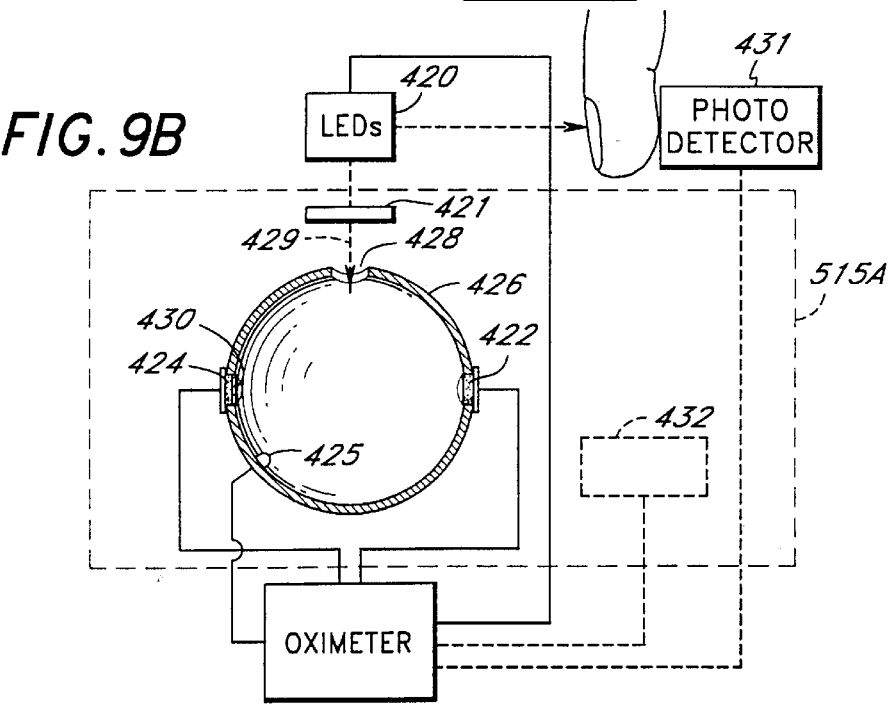

As briefly discussed above, in certain circumstances, it is useful directly to obtain information regarding the wavelength of an LED connected to an oximeter. As illustrated in FIG. 7, a wavelength detector 268 can be provided. However, a wavelength detector requires some configuration operations to be performed by the operator. In a hospital environment, it is advantageous to simplify the use of the oximeter. Accordingly, in another embodiment, each LED sensor is configured with a wavelength detection configuration. FIGS. 9A and 9B depict diagrams of possible embodiments of LED sensors configured with filters. These sensor configurations can be used to obtain the wavelength of the LED for the sensor.

As depicted in FIG. 9A, a sensor 400 comprises a transmission LED network 402, a first photodetector 404, a second photodetector 406, a diffuser 407, a beam splitter 408, an optical filter 410 and an optional optical filter 471. The transmission LED network 402, the first photodetector 404 and the second photodetector 406 all couple to an oximeter system 412. A third photodetector 413 is also depicted in dotted line to illustrate the photodetector for the oximetry measurement. This third photodetector 413 is not discussed in the following discussion which relates to the calibration portion of the oximeter probe 400. The transmission LED network 402 preferably comprises at least two LEDs, one in the red wavelength range (e.g., 660 nm) and one in the infrared wavelength range (e.g., 905 nm). Determining the wavelength of one of the LEDs in the LED network 402 using the configuration of the sensor 400 depicted in FIG. 9A is described below.

As seen in FIG. 9A, the LED network 402 transmits light 414 which first passes through the diffuser 407. The diffuser 407 is provided advantageously in the preferred embodiment in order to remove polarization of the light because the beam splitter 408 is sensitive to polarized light, and most LEDs transmit some percentage of polarized light. The light then passes to the beam splitter 408 where it is divided. The beam splitter 408 is preferably coated with a material which is partially reflective to light of the wavelength of the LEDs of interest in the LED network 402. Advantageously, the beam splitter 408 reflects approximately one-half of the light 414 and directs it to the first photodetector 404. The remainder of the light passes through the beam splitter 408 and through the filter 410 and is received by the second photodetector 406. The oximeter system 412 receives the intensity reading from the first and second photodetectors 404, 406 and utilizes the relative intensities from the first and second photodetectors 404, 406 to determine the centroid of the emission wavelength for the LEDs 402, as further explained below.

As is well understood in the art, obtaining a beam splitter to precisely divide the light by 50 percent would be costly to construct. However, it is not necessary to obtain a 50 percent split of the light because imprecision can be accommodated with calibration. In an embodiment where no second filter 411 is provided, the system can be calibrated by activating the infrared LED. This is possible because the first filter 410 is transparent to the infrared wavelength, and thus, each photodetector 404, 406 senses the same signal. In such an embodiment, the intensity outputs from the first and second photodetectors 404, 406 can be compared and equalized through calibration constants during run-time. This compensates for imprecision in the photodetectors, beam splitter 408 and diffuser 407.

In an embodiment where the infrared is not used to calibrate, the photodetectors 404, 406, the beam splitter 408 and the diffuser 407 can be calibrated prior to delivery with a passive or active coding element 415 for each device. It should be understood that the box 415 represents one or more coding elements. It should also be understood that a single coding element could be used for all of the optical devices within the box 515. Preferably, the elements provided for calibration (those within the box in dotted lines labelled 515) in this embodiment are positioned in a reusable portion of the probe such that the increased expense is not too significant.

The filter 410 may also have imprecision due to temperature sensitivity and imprecision of manufacturing process. Therefore, in order to calibrate for imprecision with respect to the filter 410 (preferably a shot glass) due to shift in temperature, a temperature detector 405 is provided in a preferred embodiment. Because temperature sensitivity in shot glass filters are well known, by detecting the temperature, the shift in filter characteristics can also be determined. With respect to the imprecision in manufacturing, a passive or active coding element 415 can be provided on the probe to provide information about the variation from a selected (ideal) filter characteristic (transition band for filter).

Another preferred embodiment utilizing a filter configuration is depicted in FIG. 9B. FIG. 9B depicts a sensor having a transmission LED network 420, a diffuser 421, a first photodetector 422, and a second photodetector 424. As in FIG. 9A, a third photodetector 431 is depicted representing the photodetector used for oximetry measurements. The first and second photodetectors 422, 424 are positioned at the interior periphery of an integrating optical sphere 426, or the like. As can be seen in FIG. 9B, the integrating optical sphere 426 has an aperture 428 through which light 429 from the LED network 420 is directed for monitoring and for wavelength determination. The light which enters the aperture is reflected about the interior of the optical sphere 426, without significant absorption. Advantageously, the interior of the integrating optical sphere is reflective to the wavelengths of the light from the LED network 420. In addition, the interior of the integrating optical sphere 426 scatters the light. Advantageously, the first and second photodetectors 422, 424 are spaced laterally across the integrating optical sphere, with the aperture 428 positioned equidistance between the first and second photodetectors 422, 424. In this manner, each of the first and second photodetectors 422, 424 receive substantially the same amount of light originating from the LED network 420.

As with the embodiment of FIG. 9A, the second photodetector 424 has an associated low pass optical filter 430, through which the light incident on the second photodetector 424 passes prior to reaching the second photodetector 424. Accordingly, like the embodiment of FIG. 9A, the second photodetector 424 in FIG. 9B receives light attenuated by the filter 430, and the first photodetector 422 receives light unattenuated by the filter 430.

As with the embodiment of FIG. 9A, as is well understood in the art, obtaining an integrating optical sphere precisely integrate the light would be costly to construct. However, again, it is not necessary to obtain a perfect integrating sphere because imprecision in the sphere (as well as in other elements) can be accommodated with calibration. For instance, the system of FIG. 9B can be calibrated by activating the infrared LED if no infrared filter (corresponding to the filter 411 in FIG. 9A) is used. This is possible because the filter 430 is transparent to the infrared wavelength, and thus, each photodetector 422, 424 senses unfiltered signal (which ideally would be the same). In such an embodiment, the intensity outputs from the first and second photodetectors 422, 424 can be compared and equalized through calibration constants during run-time. This compensates for imprecision in the photodetectors, optical sphere, and diffuser.

As with the embodiment of FIG. 9A, if the infrared is not used to calibrate, the photodetectors 422, 424, the optical sphere 426, and the diffuser 421 can be calibrated prior to delivery with passive or active coding element(s) 432 for each device.

As with the embodiment of FIG. 9A, the filter 430 may have imprecision due to temperature sensitivity and imprecision due to manufacturing. Therefore, in order to calibrate for imprecision with respect to the filter 430 (preferably a shot glass) due to shift in temperature and manufacturing tolerances, a temperature detector 425 is provided in a preferred embodiment, as with the embodiment of FIG. 9A. With respect to the imprecision in manufacturing, a passive or active coding element 432 can be provided on the probe to provide information about the variation from a selected (ideal) filter characteristic (transition band for filter).

It should also be understood, that in one embodiment, a single memory element or other passive or active element (415, 432) could be provided with enough identification capability to provide characteristic information for each of the diffuser, the photodetectors, filters, and the beam splitter (or optical sphere). For instance, a memory device or transistor network could be provided with several bits of information for device.

In the present embodiment, with red (e.g., 640–680 nm) and infrared (e.g., 900–940 nm) LEDs in the LED networks 402, 420 of FIGS. 9A and 9B, the wavelength of the red LED is the most critical for blood oximetry. Accordingly, accurate determination of the centroid operating wavelength of the red LED in the LED networks 402, 420 is desired. In this case, the filters 410, 430 advantageously are selected to partially attenuate light in the red wavelength range, and pass light in the infrared range unattenuated.

Figure 10A:
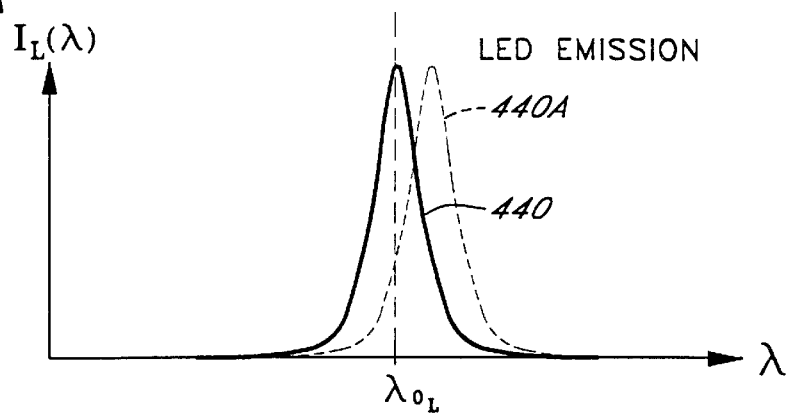
FIGS. 10A, 10B, 10C, and 10D depict graphs relating to the wavelength detection aspect of the present invention.

The principle by which the sensors of FIGS. 9A and 9B can be used to identify the wavelength of the LEDs for those sensors is now described. As well understood in the art, LEDs for use in blood oximetry and the like have an emission characteristic similar to the emission curve depicted with the curve 440 of FIG. 10A. As depicted in FIG. 10A, the ideal LED has a centroid wavelength at $\lambda_0$ (e.g., 660 nm). However, as well understood, the actual centroid wavelength for a batch of LEDs with a target centroid wavelength of $\lambda_0$ differs due to manufacturing tolerances. For instance, the emission curve may be shifted to the right as in the dotted emission curve 440A depicted in FIG. 10A. The actual centroid wavelength is significant in accurate oximetry measurements.

Figure 10B:
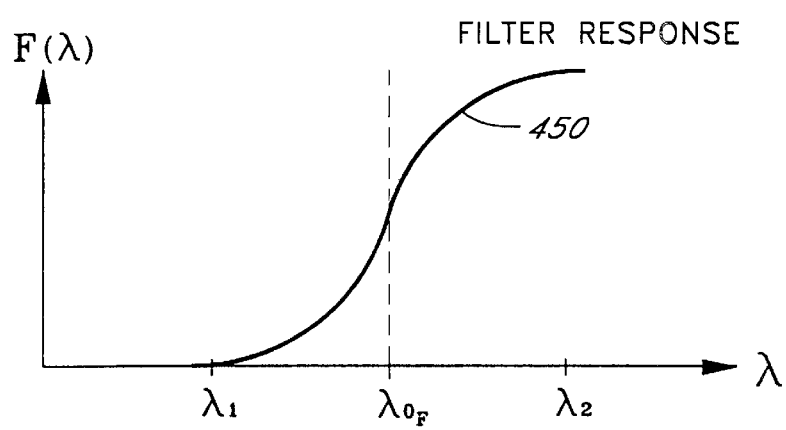

The filters 410, 430 preferably have a response as depicted by the curve 450 in FIG. 10B. With a filter chosen with the middle of its transition band selected at the target centroid wavelength, $\lambda_0$, the filter transition band advantageously extends from a lower anticipated wavelength $\lambda_1$ to an upper anticipated wavelength $\lambda_2$. The range ($\lambda_1$–$\lambda_2$)

preferably encompasses the anticipated variance in wavelengths for LEDs due to manufacturing tolerances. In other words, the manufacturing tolerance range for LEDs manufactured to have a target wavelength of $\lambda_0$, should not extend beyond the upper or lower bounds of the filter transition band.

For LEDs having a centroid wavelength in the area of the transition band of the filter, a ratio of the overall intensity detected from a sensor LED without filtering to the intensity of the same sensor LED detected with filtering provides useful information, as further explained.

Figure 10C:
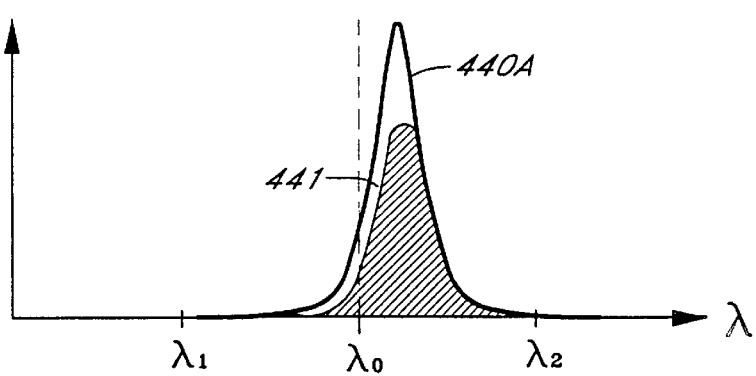

FIG. 10C is illustrative of the ratio for an LED having a wavelength just above than the target wavelength $\lambda_0$. The LED emission without filtering is represented by the LED emission curve 440A. The emission with filtering is depicted by the filtered emission curve 441. The filtered emission curve 441 represents the filter response multiplied by the LED emission without filtering as well understood for filtered emission. The significant ratio is the ratio of the area under the filtered LED emission curve 441 (illustrated with cross hatching) to the area of under the unfiltered LED emission curve 440A. It will be understood that this ratio will vary from 0–1, for LEDs with a centroid in the range $\lambda_1-\lambda_2$, and assuming the same filter response.

This ratio of the two areas can be determined from the ratio of intensities received from the photodetectors 404, 406 or 422, 424 as follows: Let the normalized intensity of the unfiltered light $I_L(\lambda)$ and the intensity of the filtered light, $I_f(\lambda)$ be represented by the following equations.

$$I_L(\lambda) = \left[\frac{1}{1+(\lambda-I_{\lambda*L})^2}\right]^2 \tag{30}$$

$$I_f(\lambda) = \left[\frac{1}{1+e^{-(\lambda-F_{\lambda*F})^2}}\right]^2$$

The energy of the unfiltered light as received by the photodetector 404, 422 can be expressed as the integral over the range of wavelengths of the LED emission as follows:

$$E(\lambda_2, \lambda_1)_{(no\ filter)} = \int_{\lambda_1}^{\lambda_2} I_L(\lambda)P(\lambda)d\lambda \tag{31}$$

where $I_L(\lambda)$ is the LED emission vs. wavelength ($\lambda$) and $P(\lambda)$ is the photodiode response vs. wavelength ($\lambda$).

For simplicity, where the photodiode response is "1" ($P(\lambda)=1$) in the range of interest ($\lambda_1-\lambda_2$) (in other words, the light emitted from the LED falls within the range of the LED), the signal of the first photodetector 404, 422 (no filter) will be as follows:

$$E(\lambda_2, \lambda_1)_{(no\ filter)} = \int_{\lambda_1}^{\lambda_2} I_L(\lambda)d\lambda \tag{32}$$

Similarly, the energy of the light received by the second photodetector 406, 424 which has passed through the filter 410, 430 can be expressed as follows:

$$E(\lambda_2, \lambda_1)_{(with\ filter)} = \int_{\lambda_1}^{\lambda_2} F(\lambda)I_L(\lambda)d\lambda \tag{33}$$

If all LEDs for a batch of sensors have the same peak emission and bandwidth in the area of interest ($\lambda_1-\lambda_2$), and can be represented by the same equation (30) except for a multiplicative constant $I_o$, then a normalized ratio of the energies can be defined as follows:

$$E_{(norm)} = \frac{E(\lambda_2, \lambda_1)_{(with\ filter)}}{E(\lambda_2, \lambda_1)_{(no\ filter)}} = \frac{I_o\int_{\lambda_1}^{\lambda_2} F(\lambda)I_L(\lambda)d\lambda}{I_o\int_{\lambda_1}^{\lambda_2} I_L(\lambda)d\lambda} \tag{34}$$

$$E_{(norm)}(\lambda) = \frac{I_o\int_{\lambda_1}^{\lambda_2} F(\lambda)I_L(\lambda)d(\lambda)}{I_o\int_{\lambda_1}^{\lambda_2} I_L(\lambda)d\lambda} = \frac{\int_{\lambda_1}^{\lambda_2} F(\lambda)I_L(\lambda)d\lambda}{constant}$$

The generalized ratio of equation (34) is a ratio of the entire area of the LED emission attenuated by filtering (designated with cross-hatching in FIG. 10C) to the area under the entire LED emission curve.

The function $E_{norm}$ is single valued and monotonic in the area ($\lambda_1-\lambda_2$) and depends only on the centroid wavelength shift of the LED with respect to the center of the transition band, $\lambda_0$, of the filter.

Figure 10D:
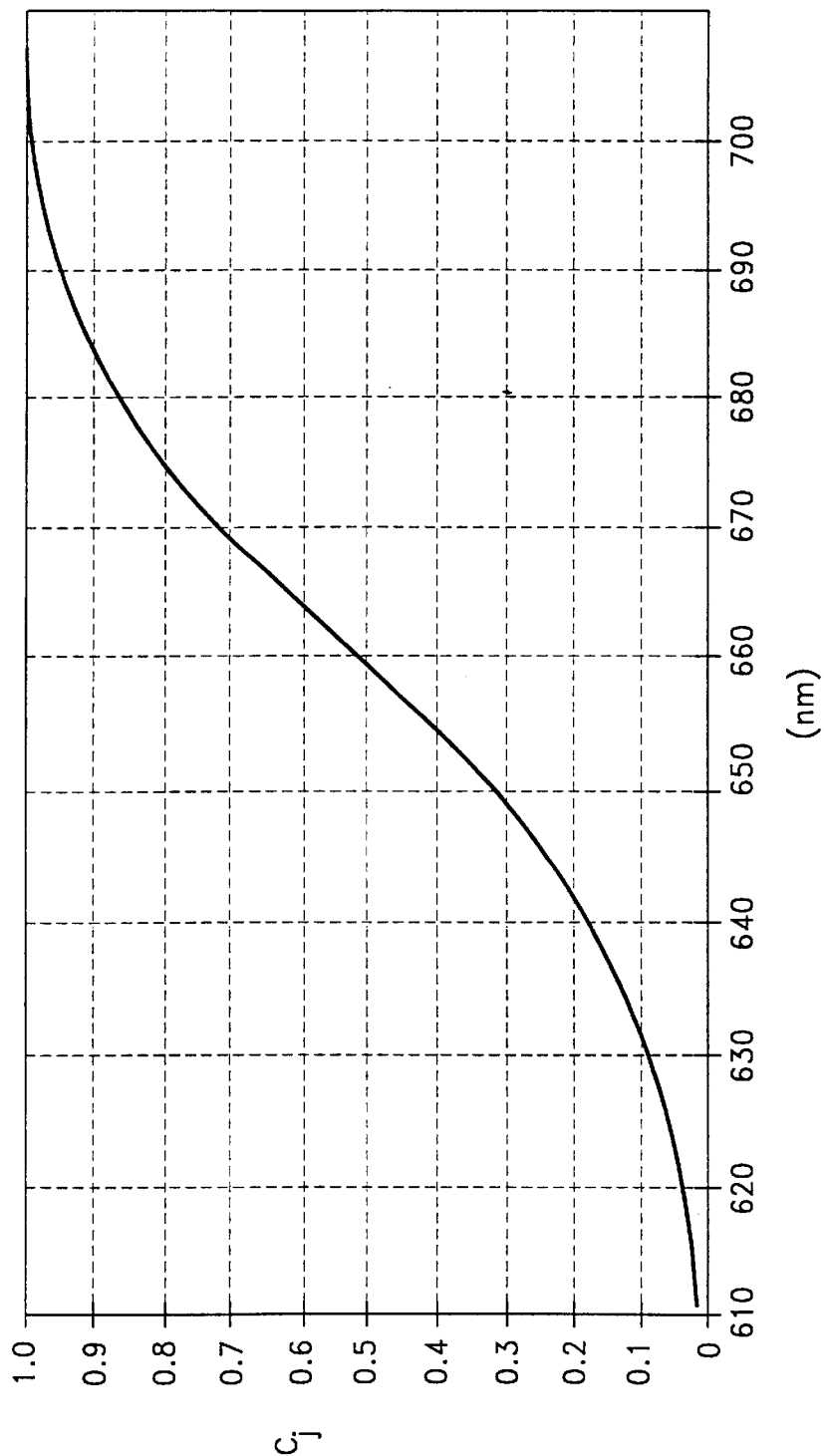

Accordingly, for a filter with a center of the transition band at $\lambda_0$, the ratio of the energy detected by second photodetector (filter present) to the energy detected by the first photodetector (filter not present) in the wavelength range ($\lambda_1-\lambda_2$), will be a value between 0 and 1. The precise ratio depends upon the centroid wavelength for the LED under test. As can be seen from FIG. 10C, as the centroid wavelength increases toward $\lambda_2$, the ratio approaches "1", and as the centroid wavelength approaches $\lambda_1$, the ratio approaches "0". This relationship is depicted in FIG. 10D for $\lambda_1=\sim610$ nm and $\lambda_2=\sim710$ nm.

In use, a ratio can be calculated to correspond to each possible LED wavelength in the range ($\lambda_1-\lambda_2$). For instance, a test batch of LEDs representing the range of wavelengths ($\lambda_1-\lambda_2$) can be used to obtain corresponding ratios of the intensity of filtered light to unfiltered light. An accurate wavelength detection device, such as a monochrometer, can be used to measure the centroid wavelength for each tested LED. The centroid wavelength can be stored for each tested LED in association with the measured ratio for each tested LED. This leads to a normalized photodiode response, which can be referenced to obtain the wavelength of an LED having an unknown wavelength in the wavelength range ($\lambda_1-\lambda_2$).

In other words, for any LED having a centroid wavelength in the range ($\lambda_1-\lambda_2$), with a sensor as depicted in FIGS. 9A and 9B, the wavelength of the LED for the sensor can be determined by taking the ratio of the intensities of the second and first photodetectors, and using the ratio to reference the normalized photodiode response to find the wavelength. In the present embodiment, this is accomplished with a look-up table stored in a memory for the oximeter system. The look-up table stores the ratio values corresponding to associated wavelength values.

Accordingly, with the sensor embodiments of FIGS. 9A and 9B, the oximeter simply continually initiates measurements for calibration purposes. The oximeter, using the method described above, calculates the ratio between the two intensities (filtered and unfiltered) and obtains the respective wavelength for the sensor. This is for testing purposes. Accordingly, the LEDs or shot glass purchased advantageously should produce a ration less than 1 and greater than 0, otherwise the LED wavelength will be undeterminable. In case the ratio equals 1 or zero, the system should either not operate or use a calibration equation that is closest to the extreme (e.g., for ratio=0, assume wavelength is 630 nm and for a ratio=1, assume wavelength is 670 nm in the present embodiment).

As mentioned above, knowledge about the precise wavelength of the red LED in an oximeter probe is generally more critical than knowledge of the precise wavelength of the infrared LED. Accordingly, the filters of the sensors of FIGS. 9A and 9B are chosen with the center of their transition band, $\lambda_o$, in the red wavelength range. As seen from the filter response curve of FIG. 10B, if the center of the transition band is in the red range, the infrared light will not be attenuated by the filter.

Figure 11:
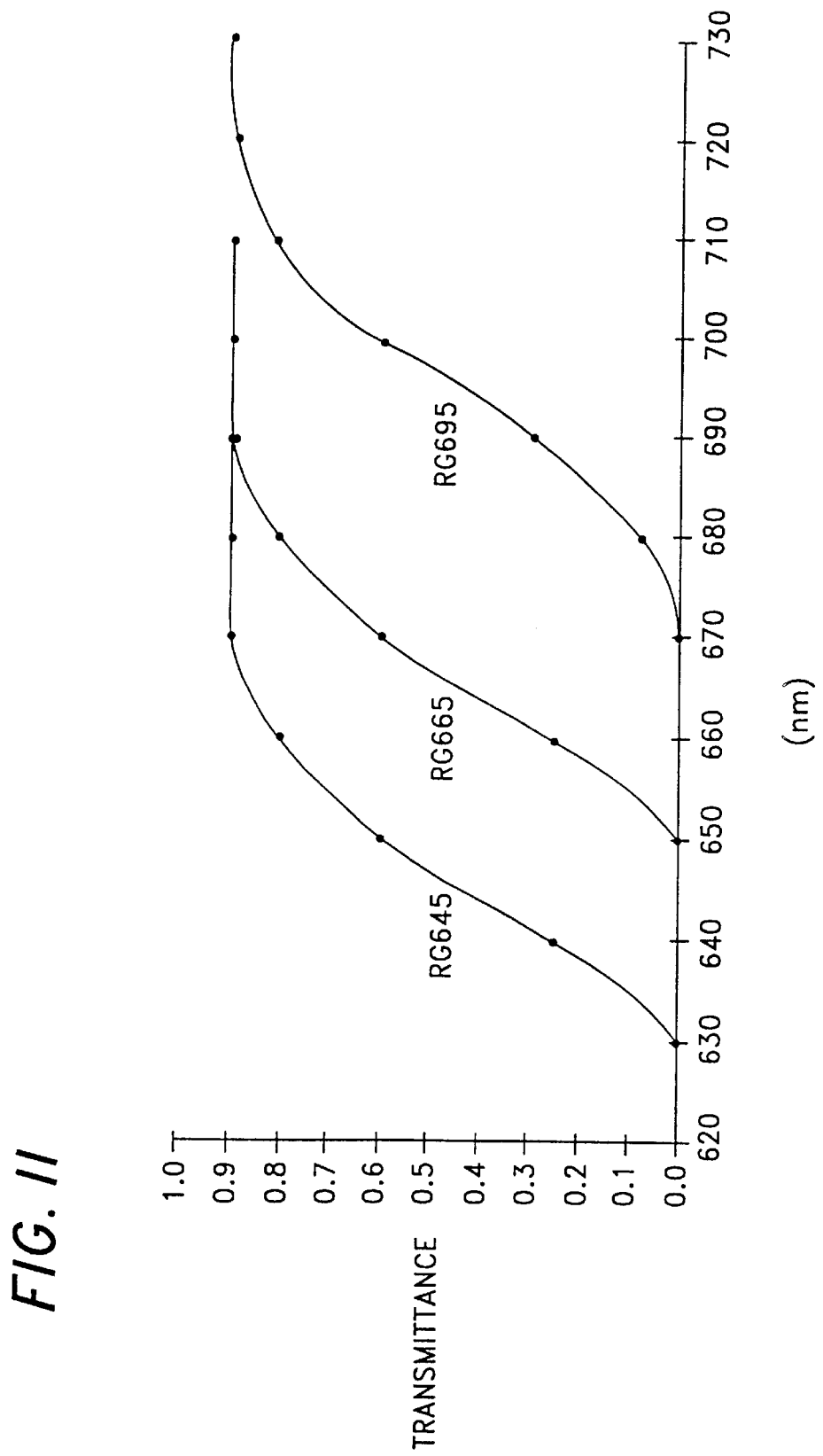
FIGS. 11 and 11A depict graphs of filter response curves for various filters in accordance with the wavelength detection aspect of the present invention.

Examples of preferable filter responses are depicted in FIG. 11. FIG. 11 depicts the response curve for three filters, adequate for the present invention, depending upon the expected wavelengths. A first filter has the center of its transition band at 645 nm, a second filter has the center of its transition band at 665 nm and a third filter has the center of its transition band at 695 nm. Other filters are also appropriate depending upon the target centroid wavelength.

Figure 11A:
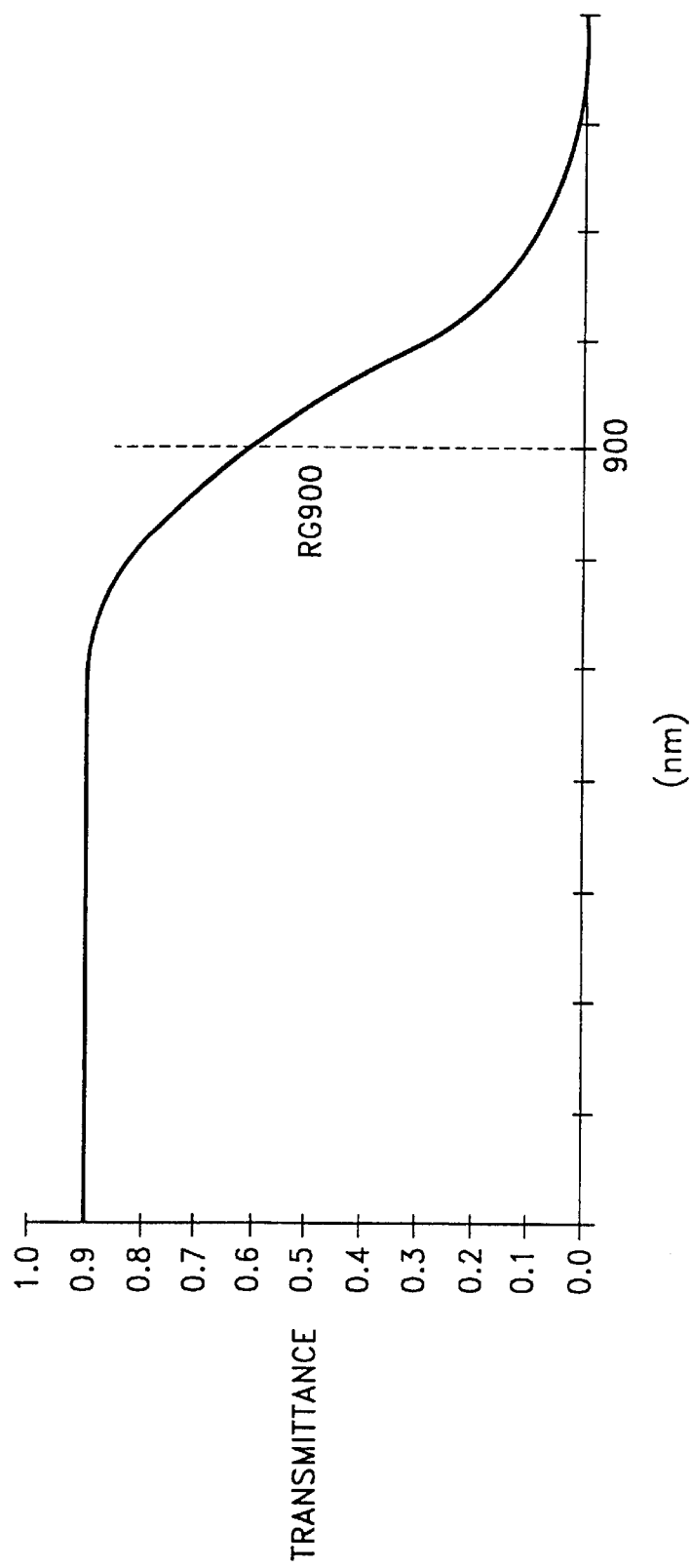

However, it should be understood that the principle explained above could also be used for the infrared LED, if the filters are chosen with the center of their transition band at $\lambda_o$ selected at the anticipated or target infrared wavelength (e.g., 905 nm). In addition, the second filter 411 (FIG. 9A) can be provided as a filter, with the center of its transition band selected at the anticipated or target infrared wavelength in order to calibrate the infrared LED as well. In other words, the second filter 411 would pass red wavelengths (would be transparent to the red LED light) and would have its transition band centered around 900 or 905 nm. Such a filter is depicted in FIG. 11A.

The wavelength detection described above could also be implemented with a sensor having only one photodetector, and a removable filter. The operator would initiate an intensity measurement as prompted by the oximeter without the filter. Then, the operator would place the filter in the light path between the LED and the photodetector, and initiate a second reading. The ratio of the second reading to the first reading provides the ratio $I_{norm}$, which is used to reference the operating wavelength.

PROBE EXAMPLES

Figure 12:
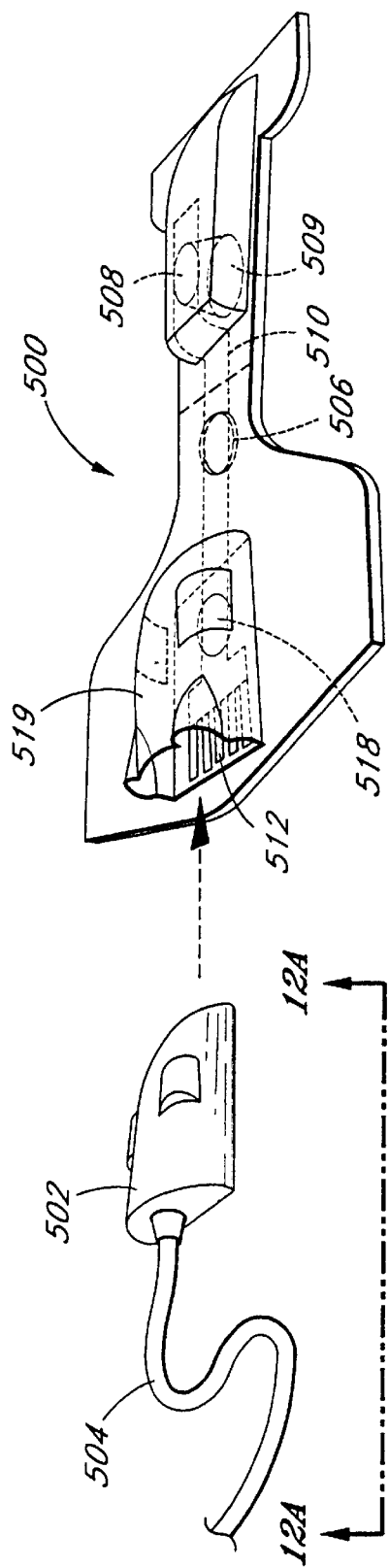
FIGS. 12–15 depict four different probe configurations for use with the present invention.
Figure 13:
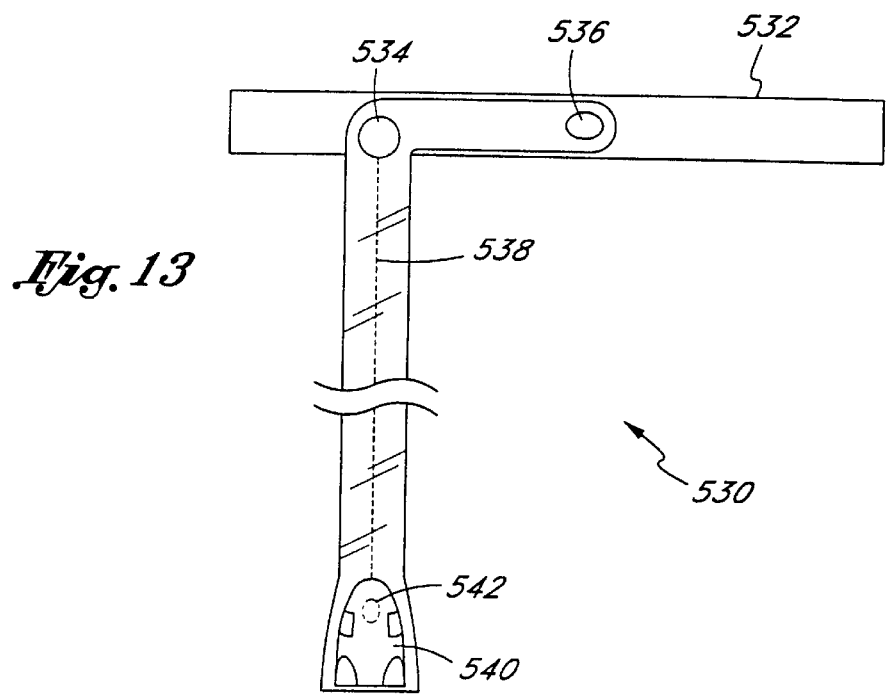
Figure 14:
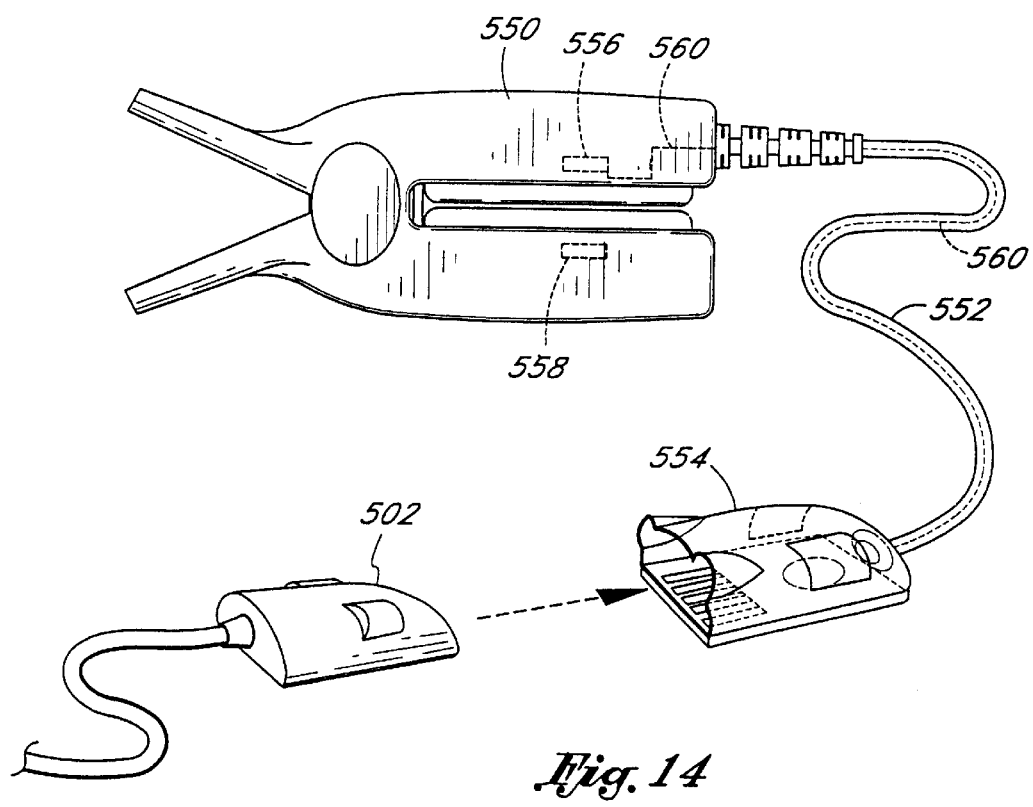

FIGS. 12–14 illustrate three different of probes used in medical monitoring of patients.

Figure 12A:
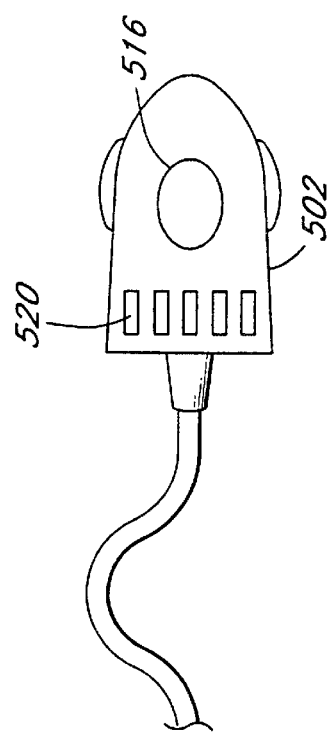
Figure 12B:
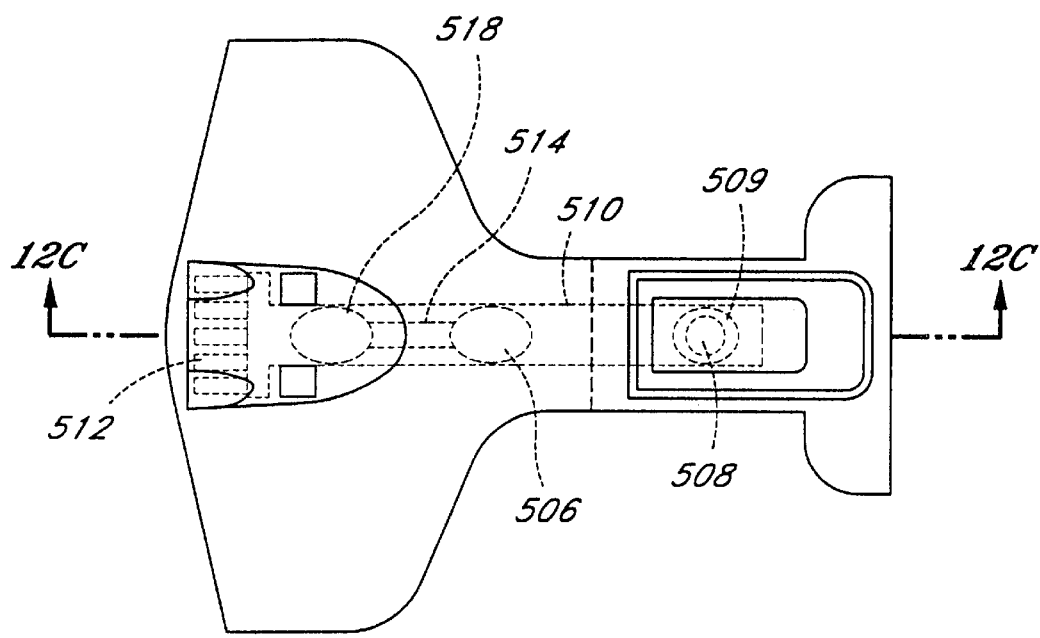
Figure 12C:
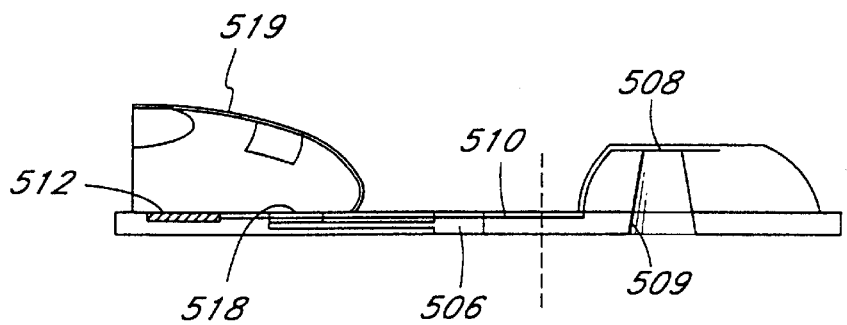

FIG. 12 depicts a wrap-around type probe 500 with an associated connector 502 coupled to a cable 504 which couples to an oximeter system (not shown in FIG. 12). FIG. 12A depicts the bottom of the connector 502. FIG. 12B depicts a bottom view of the wrap-around probe of FIG. 12, and FIG. 12C depicts a side view of the wrap-around probe of FIG. 12. The wrap around probe 500 has an LED emitter 506, a photodetector 508 at the end of a cavity 509, a flexible circuit 510, and friction electrical connection fingers 512. The probe 500 also has a connection port 519. In one embodiment, where the probe would be used for the calibratable probe of FIG. 9A, the wrap-around probe would also have a light tunnel 514 (FIG. 12B) to channel some of the light from the emitter 506 to the connector 502. In such an embodiment, all of the probe calibration elements marked in the dashed line 515, 515A in FIGS. 9A and 9B are positioned in a cavity 516 (FIG. 12A) which receives the light channeled through the light tunnel 514 and coupled to the connector 502 via an aperture 518 at the end of the light tunnel 514. As seen in FIG. 12A, electrical friction connectors 520 on the connector are configured to couple with the electrical connectors 512 of the wrap-around probe 500. The flexible circuit connects the emitters 506 and the detector 508 to the connection fingers 512.

In use, the wrap-around probe is placed on the digit of a patient, and the photodetector 508 is positioned opposite the emitter 506 so as to receive light from the emitter 506 attenuated by transmission through a fleshy medium.

FIG. 13 depicts another embodiment of a wrap-around probe 530 for medical monitoring of infants. The probe has a first flexible portion 532 configured to be wrapped about the digit of a neonate attached to the first flexible portion 532 is a second flexible member carrying emitters 534 (LEDs) and photodetector 536. In one embodiment where the calibration probe of FIG. 9A is implemented with the probe of FIG. 13, a fiber optic 538 is provided to carry part of the light from the emitter 534 to the connector port 540 of the probe 530. In this manner, the same connector 502 having a photodetector can be utilized with the infant style probe of FIG. 13. Alternatively, a light channel or tunnel could be used instead of the fiber optic to carry a portion of the light from the emitter 534 to the connector port 540. The same connector 542 is used for the neonatal probe 530. Accordingly, as with the embodiment of FIG. 12, all of the calibration elements within the dotted box 515, 515A of FIGS. 9A and 9B are positioned within the connector 502.

FIG. 14 depicts yet another probe for use in medical monitoring. The probe of FIG. 14 comprises a clip-on probe 550 which couples via a cable 552 to a connector port 554 which is the same as the connector port 540 of FIG. 13 and the connector port 519 of FIG. 12. The clip-on probe carries emitters 556 and a photodetector 558. With this embodiment, some light from the emitters 556 enters a fiber optic 560 which channels light to the connector port 554 as in the embodiment of FIG. 13. Again, the probe calibrations elements within the same connector 502 are preferably contained within the connector 502 which is advantageously the same as the connector for the embodiments of FIGS. 12 and 13.

Figure 15C:
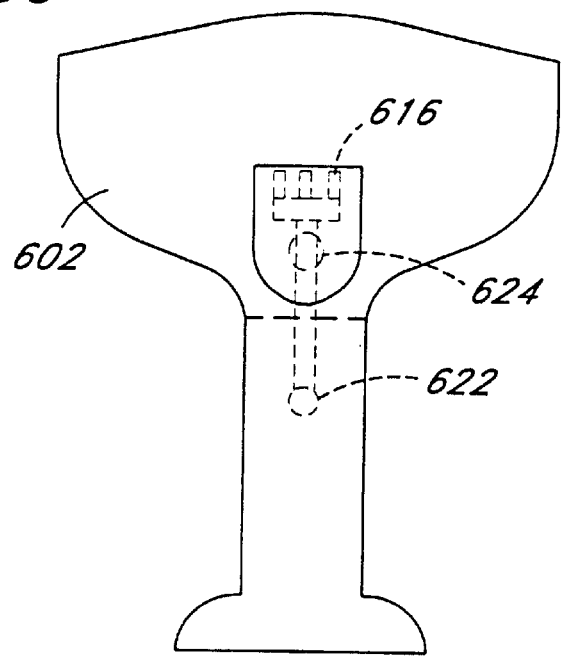
Figure 15D:
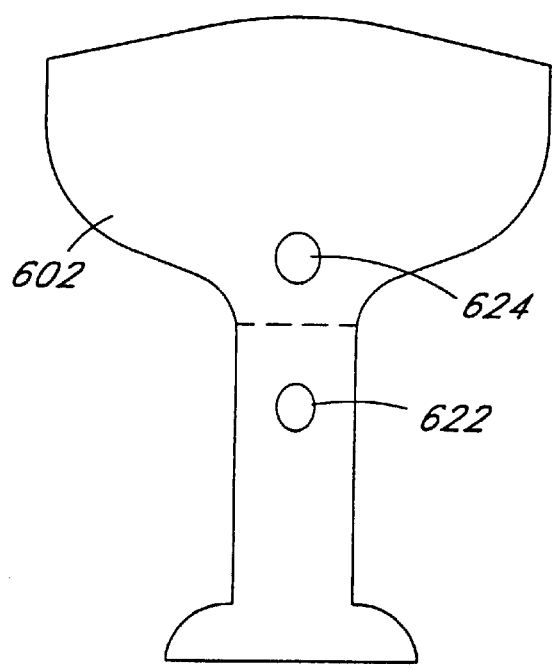

FIGS. 15–15D depict yet another embodiment of a wrap-around probe 600 comprising a flexible wrap portion 602 with an associated connector 604 coupled to a cable 506 which couples to an oximeter system (not shown in FIG. 15). FIG. 15 depicts a perspective view of the entire probe 600. FIG. 15A depicts the underside of the connector 604. FIG. 15C depicts a top view of the wrap portion 602 and FIG. 15D depicts a bottom view of the wrap portion 602. The connector 604 has two portions: an emitter portion 610 and a connection portion 612. The emitter portion 610 advantageously contains the emitters (such as LEDs) for the selected wavelengths. This emitter portion 610 can be reused for a period of time, preferably weeks to months, thereby allowing for further reduced cost of the wrap-around portion 602 which is disposable after each use. In other words, emitters need not be provided for each wrap portion 602. Yet, the emitter portion 610 is removably coupled to the connection portion 612 of the connector 604, allowing the connection portion 612 to be reusable for a much longer period of time.

In this embodiment, the wrap portion 602 is flexible and disposable after each use with a very low cost. The wrap portion has a flexible layer 626 made from polymer or other flexible materials and has a connector port 614 on the flexible layer 626. The connector port 614 has electrical finger friction connectors 616 which are adapted to couple to electrical finger friction connectors 620 (FIG. 15A) on the bottom of the connection portion 612 of the connector 604. The electrical finger friction connectors 616 for the wrap portion 602 couple to a flexible circuit 618 which connects to a detector 622 which is shielded (not shown) for the detector 622. Two of the connections couple to the detector 622 and the third is for the shield which is preferably a conventional Faraday shield to protect the detector from electromagnetic interference and the like.

The wrap around probe 600 has an aperture 624 that provides a window for the transmission of light energy from the emitters in the emitter portion 610. The emitters are positioned to transmit light through an aperture 628 (FIG. 15A) in the emitter portion 610 which is configured to match with the aperture 624 in the wrap portion 602 when the connector 604 is positioned in the connection port 614. Thus, the light transmits from the emitters in the emitter portion 610 through the aperture 628 in the emitter portion 610 and through the aperture 624 in the wrap portion 602 when the connector 604 is inserted into the connector port 614 and the emitters are activated.

In use, the wrap portion 602 is wrapped around a digit of the patient (e.g., a finger) and the detector 622 is positioned to receive light transmitted through the aperture 624 and through at least a portion of the digit. For instance, the wrap portion 602 can be wrapped around a finger in a manner that the detector 622 is opposite the aperture 624 from which light energy is transmitted.

In one embodiment, the probe 600 is used for the calibratable probe of FIGS. 9A and 9B. In this embodiment, the connection portion 612 has the elements in the dotted boxes 515 and 515A of FIGS. 9A and 9B positioned in the connection portion 612. In this manner, the calibration elements are reusable, yet work with the LEDS in the emitter portion 610 to form a calibratable embodiment. In such an embodiment, the emitters are positioned in the emitter portion 610 such that the majority of the light energy transmits through the aperture 628 and that some light energy transmits to a light aperture 620 in the end of the connection portion 612 (FIG. 15B). The connection portion 612 contains the calibration elements depicted in the boxes 515 and 515A (FIGS. 9A AND 9B) housed in the connection portion 612.

FIG. 15B depicts an end view of the connection portion 612 depicting the light channel 620 and two electrical connector 613A, 613B which provide connections for LEDs (red and infrared connected back-to-back in the present embodiment) in the emitter portion.

It will be understood that the apparatus and method of the present invention may be employed in any circumstance where a measurement of transmitted or reflected energy is required, including but not limited to measurements taken on a finger, an earlobe, or a lip. Thus, there are numerous other embodiments which will be obvious to one skilled in the art. Furthermore, the apparatus and method of the present invention may be employed for any LED application that is wavelength sensitive. The present invention may thus be embodied in other specific forms without departing from its spirit or essential characteristics. The described embodiments are to be considered in all respects only as illustrative and not restrictive. The scope of the invention is, therefore, indicated by the following appended claims. All changes which come within the meaning and range of equivalency of these claims are to be embraced within their scope.

What is claimed is:

1. An oximeter sensor system comprising:
    a cable;
    a substantially rigid connector connected to an end of the cable, wherein the substantially rigid connector includes an electronic element housing an emitter or a detector of a probe; and
    a flexible wrap portion comprising
        an adhesive side in an area of the emitter and the detector, and
        a substantially rigid connection port shaped to receive the substantially rigid connector in a releasably securable manner,
    wherein the adhesive side provides proper placement of the emitter and the detector with respect to the measurement site when the flexible wrap portion is applied to a wearer of the probe.

2. The oximeter sensor system of claim 1, wherein the emitter transmits through an aperture in the substantially rigid connector.

3. The oximeter sensor system of claim 1, wherein the flexible wrap portion is disposable.

4. A probe for returning a signal representative of light attenuated by transmission through a measurement site and representative of a physiological parameter, the probe comprising:
    a cable;
    a first housing having a first shape, wherein the first housing includes a releasable attachment mechanism and an emitter electrically connected to the cable;
    a bandage;
    a second housing attached to the bandage and having a second shape configured to receive the first shape and secure the first housing to the bandage through attachment to the releasable attachment mechanism; and
    a detector electrically connected to the cable which receives light from the emitter attenuated by transmission through a measurement site, wherein the bandage includes an adhesive portion in an area of the emitter and the detector to position the emitter and the detector over the measurement site.

5. The probe of claim 4, wherein the detector is housed within the bandage.

6. The probe of claim 4, wherein the bandage is disposable.

7. The probe of claim 4, wherein the releasable attachment mechanism of the first housing releasably attaches to the second housing.

8. The probe of claim 4, wherein the first housing comprises a rigid shape.

9. The probe of claim 4, wherein the first housing comprises an aperture through which the emitter transmits light.

10. The probe of claim 4, wherein the second housing comprises a rigid shape.

11. The probe of claim 4, wherein at least one of the first and second housings comprises a plastic material.

12. A method of applying an oximeter probe to a measurement site, the method comprising:
    providing a rigid connector having an electronic component;
    providing a rigid connection port including a receptacle, wherein the rigid connection port is attached to a wrap;
    releasably plugging the rigid connector into the receptacle in a manner which provides proper placement of the electronic component with respect to the wrap; and
    adhering the wrap in at least an area of the emitter and the detector to a measurement site.

13. The method of claim 12, wherein the electronic component comprises an emitter portion.

14. The method of claim 12, wherein the rigid connector is reusable.

15. The method of claim 12, wherein the wrap is disposable.

* * * * *

UNITED STATES PATENT AND TRADEMARK OFFICE
CERTIFICATE OF CORRECTION

PATENT NO. : 6,678,543 B2
DATED : January 13, 2004
INVENTOR(S) : Mohamed K. Diab et al.

It is certified that error appears in the above-identified patent and that said Letters Patent is hereby corrected as shown below:

Column 27, line 58 to Column 28, line 7,
Replace the text of claim 1 with the following claim:

1. An oximeter sensor system comprising:
   at least one emitter;
   a detector;
   a cable;
   a substantially rigid connector connected to an end of the cable, wherein the substantially rigid connector includes the emitter; and
   a flexible wrap portion comprising
      a connection port side;
      an adhesive side opposite the connection port side, wherein the adhesive side includes adhesive in an area underneath of the emitter and the detector, and
      a substantially rigid connection port on the connection port side shaped to receive the substantially rigid connector in a releasably securable manner,
      wherein the adhesive side provides proper placement of the emitter and the detector with respect to a measurement site when the flexible wrap portion is applied to a wearer of the probe.

Column 28,
Lines 13-32, replace the text of claim 4 with the following claim:

4. A probe for returning a signal representative of light attenuated by transmission through a measurement site and representative of a physiological parameter, the probe comprising:
   a cable;
   a first housing having a first shape, wherein the first housing includes a releasable attachment mechanism and an emitter electrically connected to the cable;
   a bandage including a first side and a second side;
   a second housing attached to the bandage on the first side and having a second shape configured to receive the first shape and secure the first housing to the bandage through attachment to the releasable attachment mechanism; and
   a detector electrically connected to the cable which receives light from the emitter attenuated by transmission through a measurement site, wherein the second side of the bandage includes adhesive underneath an area of the emitter and the detector on the first side, wherein the adhesive positions the emitter and the detector over the measurement site.

UNITED STATES PATENT AND TRADEMARK OFFICE
CERTIFICATE OF CORRECTION

PATENT NO. : 6,678,543 B2
DATED : January 13, 2004
INVENTOR(S) : Mohamed K. Diab et al.

It is certified that error appears in the above-identified patent and that said Letters Patent is hereby corrected as shown below:

Column 28 (cont'd),
Lines 48-61, replace the text of claims 12-13 with the following claim:

12. A method of applying an oximeter probe to a measurement site, the method comprising:
   providing a first electronic component;
   providing a rigid connector having a second electronic component;
   providing a rigid connection port including a receptacle, wherein the rigid connection port is attached to a first side of a wrap, wherein the first side of the wrap is opposite a second side of the wrap;
   releasably plugging the rigid connector into the receptacle in a manner which provides proper placement of the second electronic component with respect to the wrap; and
   adhering the second side of the wrap in at least an area underneath the first and second electronic components to attach the wrap to a measurement site.
13. The method of claim 12, wherein the second electronic component comprises an emitter portion.

Signed and Sealed this

Twenty-eighth Day of June, 2005

JON W. DUDAS
*Director of the United States Patent and Trademark Office*

UNITED STATES PATENT AND TRADEMARK OFFICE
CERTIFICATE OF CORRECTION

PATENT NO. : 6,678,543 B2
APPLICATION NO. : 10/005711
DATED : January 13, 2004
INVENTOR(S) : Mohamed K. Diab et al.

It is certified that error appears in the above-identified patent and that said Letters Patent is hereby corrected as shown below:

At Column 23, Line 30, please delete "
$$I_L(\lambda) = \left[\frac{1}{1+(\lambda-I_{\lambda\bullet L})^2}\right]^2 \qquad I_f(\lambda) = \left[\frac{1}{1+e^{-(\lambda-F_{\lambda\bullet F})^2}}\right]^2$$
" and insert --
$$I_L(\lambda) = \left[\frac{1}{1+(\lambda-I_{\lambda_{o_L}})^2}\right]^2 \qquad I_f(\lambda) = \left[\frac{1}{1+e^{-(\lambda-F_{\lambda_{o_F}})^2}}\right]^2$$
--.

Column 27, line 58 to Column 28, line 7,
Replace the text of claim 1 with the following claim:

1. An oximeter sensor system comprising:
   at least one emitter,
   a detector;
   a cable;
   a substantially rigid connector connected to an end of the cable, wherein the substantially rigid connector includes the emitter; and
   a flexible wrap portion comprising
      a connection port side;
      an adhesive side opposite the connection port side, wherein the adhesive side includes adhesive in an area underneath the emitter and the detector, and
      a substantially rigid connection port on the connection port side shaped to receive the substantially rigid connector in a releasably securable manner,
      wherein the adhesive side provides proper placement of the emitter and the detector with respect to a measurement site when the flexible wrap portion is applied to a wearer of the probe.

This certificate supersedes the Certificate of Correction issued June 28, 2005.

Signed and Sealed this
Thirtieth Day of October, 2012

David J. Kappos
*Director of the United States Patent and Trademark Office*

CERTIFICATE OF CORRECTION (continued)
U.S. Pat. No. 6,678,543 B2

Column 28, lines 13-32,
Replace the text of claim 4 with the following claim:

4. A probe for returning a signal representative of light attenuated by transmission through a measurement site and representative of a physiological parameter, the probe comprising:
   a cable;
   a first housing having a first shape, wherein the first housing includes a releasable attachment mechanism and an emitter electrically connected to the cable;
   a bandage including a first side and a second side;
   a second housing attached to the bandage on the first side and having a second shape configured to receive the first shape and secure the first housing to the bandage through attachment to the releasable attachment mechanism; and
   a detector electrically connected to the cable which receives light from the emitter attenuated by transmission through a measurement site, wherein the second side of the bandage includes adhesive underneath an area of the emitter and the detector on the first side, wherein the adhesive positions the emitter and the detector over the measurement site.

Column 28 (cont'd), Lines 48-61,
Replace the text of claims 12-13 with the following claim:

12. A method of applying an oximeter probe to a measurement site, the method comprising:
   providing a first electronic component;
   providing a rigid connector having a second electronic component;
   providing a rigid connection port including a receptacle, wherein the rigid connection port is attached to a first side of a wrap, wherein the first side of the wrap is opposite a second side of the wrap;
   releasably plugging the rigid connector into the receptacle in a manner which provides proper placement of the second electronic component with respect to the wrap; and
   adhering the second side of the wrap in at least an area underneath the first and second electronic components to attach the wrap to a measurement site.

13. The method of claim 12, wherein the second electronic component comprises an emitter portion.